United States Patent
Kao et al.

(10) Patent No.: US 9,212,177 B2
(45) Date of Patent: Dec. 15, 2015

(54) ANTIVIRAL COMPOUNDS AND METHODS OF MAKING AND USING THEREOF

(75) Inventors: Yi Tsun Richard Kao, Hong Kong (CN); Dan Yang, Hong Kong (CN); Kwok-Yung Yuen, Hong Kong (CN)

(73) Assignee: Versitech Limited, Hong Kong (HK)

( * ) Notice: Subject to any disclaimer, the term of this patent is extended or adjusted under 35 U.S.C. 154(b) by 884 days.

(21) Appl. No.: 12/850,806

(22) Filed: Aug. 5, 2010

(65) Prior Publication Data

US 2011/0212975 A1  Sep. 1, 2011

Related U.S. Application Data

(60) Provisional application No. 61/231,431, filed on Aug. 5, 2009, provisional application No. 61/349,525, filed on May 28, 2010, provisional application No. 61/349,565, filed on May 28, 2010.

(51) Int. Cl.
*A61K 31/496* (2006.01)
*C07D 413/06* (2006.01)

(52) U.S. Cl.
CPC .......... *C07D 413/06* (2013.01); *A61K 31/496* (2013.01)

(58) Field of Classification Search
None
See application file for complete search history.

(56) References Cited

U.S. PATENT DOCUMENTS

| 7,196,080 | B2 * | 3/2007 | Iwata et al. | 514/227.5 |
| 2004/0097734 | A1 * | 5/2004 | Gerlach et al. | 544/323 |
| 2012/0149715 | A1 * | 6/2012 | Kao et al. | 514/254.04 |

OTHER PUBLICATIONS

Kang et al. Solution-phase combinatorial synthesis of isoxazolines and isoxazoles using [2+] cycloaddition reaction of nitrile oxides. Tetrahydron Letters, 42, 2001, 1057-1060.*
Patani et al. "Bioisosterism: a rational approach in drug design." Chem. Rev. 1996, 96(8), pp. 3147-3176.*
Asproni et al. Synthesis and pharmacological evaluation of 1-[(1,2-diphenyl-1H-4-imidazolyl)methyl]-4-phenylpiperazines with clozapine-like mixed activities at dopamine D2 serotonin, and GABAa receptors. J. Med. Chem. 2002, 45, 4655-4668.*
Williams et al. (Foye's Principles of Medicinal Chemistry, $5^{th}$ edition, pp. 50 and 59-61, 2002).*
Aquzzi and O\Connor, "Protein aggregation diseases: pathogenicity and therapeutic perspectives", Nature Reviews Drug Discovery, 9:237-248 (2010).
Cortesi, et al., "Sugar cross-linked gelatin for controlled release: microspheres and disks", Biomaterials, 19:1641-1649 (1998).
GenBank Accession No. AAA43467, "Nucleopretein[Influenza A virus (A/Puerto Rico/8/1934(Cambridge)(HiNi))]", one page, submitted May 25, 2005, first published May 25, 2006, accessed Aug. 10, 2011.

(Continued)

*Primary Examiner* — Anna Pagonakis
(74) *Attorney, Agent, or Firm* — Pabst Patent Group LLP

(57) ABSTRACT

Compounds which exhibit antiviral activity, particularly against influenza virus, and methods of making and using thereof are described herein. In one embodiment, the compounds are heterocyclic amides containing piperazine and isoxazole rings and optionally substituted with one or more substituents. The compounds can be formulated with one or more pharmaceutically acceptable excipients to form compositions suitable for enteral or parenteral administration. The compounds are preferably used to treat or prevent Influenza A infections, such as H1N1, H2N2, H3N2, H5N1, H7N7, H1N2, H9N2, H7N2, H7N3, and H10N7.

19 Claims, 10 Drawing Sheets

(56) References Cited

OTHER PUBLICATIONS

GenBank Accession No. AAF02400, "Nucleoprotein [Influenza A virus(A/chicken/Hong Kong/915/97(H5N1))]", one page, submitted Oct. 15, 1998, first published Oct. 16, 1999, accessed Aug. 10, 2011.

GenBank Accession No. AAZ38620, "Nucleocapsid protein[Influenza A virus(A/New York/392/2004(H3N2))]", one page, submitted Dec. 21, 2004, first published Aug. 1, 2005, accessed Aug. 10, 2011.

GenBank Accession No. AY856864, "Influenza A virus (A/duck/Shandong/093/2004(H5N1)) segment 5, complete sequence", one page, submitted Dec. 15, 2004, first published Feb. 6, 2005, accessed Aug. 10, 2011.

Wang, "Protein aggregation and its inhibition in biopharmaceutics", Int J Pharm. 289:1-30 (2005).

* cited by examiner

ANTIVIRAL COMPOUNDS AND METHODS OF MAKING AND USING THEREOF

CROSS REFERENCE TO RELATED APPLICATIONS

This application claims priority to U.S. Ser. No. 61/231,431, entitled "Antiviral Compounds", filed on Aug. 5, 2009; U.S. Ser. No. 61/349,525, entitled "Compounds and Methods for the Treatment of Viral Infections", filed on May 28, 2010; and U.S. Ser. No. 61/349,565 entitled "Compounds and Methods for the Treatment of Proliferative Diseases", filed on May 28, 2010, all of which are incorporated herein by reference in their entirety.

FIELD OF THE INVENTION

This invention is in the field of small molecules which have antiviral activity, particularly against influenza, and methods of making and using thereof.

BACKGROUND OF THE INVENTION

Influenza is caused by an RNA virus of the orthomyxoviridae family. There are three types of influenza viruses: A, B and C. Influenza A viruses infect mammals (e.g. humans, pigs, ferrets, horses) and birds. Influenza A viruses are a global health concern, and have been responsible for three major pandemics that have killed over 50 million people worldwide since 1900. For example, the devastating "Spanish flu" (H1N1 influenza A virus) in 1918 killed more than twenty million people worldwide. Subsequent pandemics, including the Asian flu pandemic in 1957 (H2N2), the Hong Kong flu pandemic in 1968 (H3N2), the re-emergence of H1N1 (Russian flu) in 1970, along with the avian flu virus H5N1 in 1997 and 2003, suggest that pandemic influenza or possible bioterrorist attacks with flu viruses remains a major threat to global health and safety. Despite the profound effects of influenza viruses on public health throughout history, the standard treatments for influenza infections still remain inadequate.

The most common targets for small molecule-based therapeutics to combat influenza virulence include the proton-selective M2 ion channel and the protein neuramidase (NA). The M2 ion channel is integral to the maintenance of the viral envelope of the influenza A virus, while NA promotes budding of nascent viral particles from the host cell. Resistance is common among inhibitors directed at both targets, and has become widespread in clinical isolates. Almost 100% of the 2008 influenza H1N1 virus (swine flu) samples were resistant to the neuramidase inhibitor oseltamivir (Tamiflu), while more than 90% of the H3N2 viruses were resistant to the M2 channel blocker adamantanes.

Besides resistance, factors including mode of administration and environmental impact affect the development of effective influenza treatments. For instance, Zanamivir (Relenza) can only be administered by inhalation and may not reach infected lung tissue that is poorly aerated. Further, the widely used and stockpiled drug Oseltamivir is not degraded during the course of normal sewage treatment and thus poses environmental concerns.

There exists a need for antiviral compounds that inhibit influenza replication, reduce virulence of the influenza infection, and/or prevent influenza infection.

Therefore, it is an object of the invention to provide antiviral compounds that effectively treat or prevent viral infections, particularly influenza infections, methods of making the compounds, and methods of using the compounds.

SUMMARY OF THE INVENTION

Compounds having antiviral activity, particularly against influenza, and methods of making and using the compounds are described herein. In one embodiment, the compounds have formulae I-VI or pharmaceutically acceptable salts thereof.

In particular embodiments, the NP inhibitors have the structure of formula I:

$$Ar^1-Y-Ar^2-X-W-Z-Ar^3 \quad \text{(Formula I)}$$

wherein $Ar^1$, $Ar^2$, and $Ar^3$ are each independently substituted or unsubstituted aryl or heteroaryl groups;

X, Y, and Z are independently absent (i.e., a direct bond) or selected from —C(=O)—, —S(=O)—, —SO$_2$—, —N(R$_1$)—, —C(R$_2$)=C(R$_3$)—, and —[C(R$_4$R$_5$)]$_n$—, wherein n is 0 to 6 and wherein $R_1$-$R_5$ are each independently selected from hydrogen; hydroxyl; halogen; substituted or unsubstituted amino; —CN; —NO$_2$; —COOH; carboxylate; —COR, —COOR, or —CON(R)$_2$; substituted or unsubstituted aryl, such as phenyl or benzyl; substituted or unsubstituted, linear or branched $C_1$-$C_6$ alkyl; substituted or unsubstituted, linear or branched $C_1$-$C_6$ alkenyl; substituted or unsubstituted, linear or branched $C_1$-$C_6$ alkynyl; substituted or unsubstituted $C_3$-$C_6$ cycloalkyl or cycloalkenyl; or substituted or unsubstituted, linear and branched $C_1$-$C_6$ alkoxy; and W is a linear group or a 5-7-membered substituted or unsubstituted cyclic or heterocyclic group (Cy).

In some embodiments, $Ar^1$ is substituted with hydrogen, hydroxyl, nitro, amino, or azide; $Ar^2$ is substituted with a methyl group; X is C=O; Y and Z are absent; Cy is piperazine; and $Ar^3$ is substituted with a halo group, a nitro group, or combinations thereof.

In some embodiments, Cy is a substituted 5-7-membered unsaturated ring containing 2 nitrogen atoms, wherein one nitrogen atom is bonded to X and the other nitrogen atom is bonded to Z.

In a preferred embodiment, Cy is a substituted piperazine, wherein N1 is bonded to X and N4 is bonded to Z.

In one embodiment, the compound is not nucleozin.

In some embodiments, the NP inhibitors have the structure of formula II:

(formula II)

$$Ar^1 \overset{Y}{\underset{Q-T}{\overset{\displaystyle X-A-\left(\phantom{X}\right)_g\!\!\!\!\!_m-D-Z-Ar^3}{\bigg|}}} R_4 \quad R$$

wherein $Ar^1$ and $Ar^3$ are each independently substituted or unsubstituted aryl or heteroaryl groups;

X, Y, and Z are independently absent or selected from the group consisting of —C(=O)—, —S(=O)—, —SO$_2$—, —N(R$_{10}$)—, —C(R$_{11}$)=C(R$_{12}$)—, and —[C(R$_{13}$R$_{14}$)]$_n$—, n, g, and m are independently 0 to 6;

T, Q, and R are independently selected from C(R$_8$R$_9$), nitrogen, oxygen, phosphorous, silicon, sulfur, and arsenic;

A and D are each independently CR$_{15}$R$_{16}$ or NR$_{17}$;

wherein $R_4$ and $R_8$-$R_{17}$ are independently selected from hydrogen; halo; hydroxyl; substituted or unsubstituted, linear or branched $C_1$-$C_6$ alkyl; substituted or unsubstituted, linear or branched $C_1$-$C_6$ alkenyl; substituted or unsubstituted, linear or branched $C_1$-$C_6$ alkynyl; or substituted or unsubstituted, linear or branched $C_1$-$C_6$ alkoxy; amino; azide; cyano; nitro; nitrile; isonitrile; amide; carboxylate; urea; guanidine; isocyanate; isothiocyanate; and thioether; or wherein —$CR_{15}R_{16}$—, —$NR_{17}$—, or combinations thereof, when taken together with the optional bridging methylene groups, form a 5-8-membered cyclic structure.

In some embodiments, $Ar^1$ is substituted with hydrogen, hydroxyl, nitro, amino, or azide; X is —C=O; Y and Z are absent, and $Ar^3$ is substituted with a halo group, a nitro group, or a combination of a halo and nitro group.

In a preferred embodiment, $R_4$ is methyl.

In some embodiments, Q is carbon, T is oxygen, and R is nitrogen.

In some embodiments, g and m are 1 and A and D are $NR_{17}$, wherein A-D defines a piperazine.

In some embodiments, the NP inhibitors have the structure of formula III:

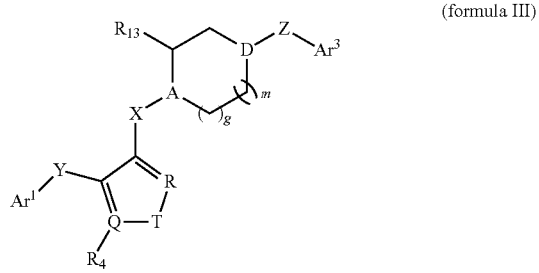

(formula III)

wherein $Ar^1$ and $Ar^3$ are each independently substituted or unsubstituted aryl or heteroaryl groups;

X, Y, and Z are independently absent or selected from the group consisting of —C(=O)—, —S(=O)—, —SO$_2$—, —N(R$_{10}$)—, —C(R$_{11}$)=C(R$_{12}$)—, and —C(R$_{14}$R$_{15}$)$_n$—, n, g, and m are independently 0 to 6;

A, D, T, Q, and R are independently selected from C($R_8R_9$), nitrogen, oxygen, phosphorous, sulfur, silicon, and arsenic;

wherein $R_4$ and $R_8$-$R_{15}$ are independently selected from hydrogen; halo; hydroxyl; substituted or unsubstituted, linear or branched $C_1$-$C_6$ alkyl; substituted or unsubstituted, linear or branched $C_1$-$C_6$ alkenyl; substituted or unsubstituted, linear or branched $C_1$-$C_6$ alkynyl; or substituted or unsubstituted, linear or branched $C_1$-$C_6$ alkoxy; amino; azide; cyano; nitro; nitrile; isonitrile; amide; carboxylate; urea; guanidine; isocyanate; isothiocyanate; and thioether.

In some embodiments, $Ar^1$ is substituted with hydrogen, hydroxyl, nitro, amino, or azide; X is C=O; Y and Z are absent, and $Ar^3$ is substituted with a halo group, a nitro group, or a combination of a halo and nitro group.

In a preferred embodiment, Q is carbon, T is oxygen, and R is nitrogen.

In some embodiments, A and D are nitrogen.

In some embodiments, $R_4$ and $R_{13}$ are independently hydrogen or methyl. In preferred embodiments, $R_4$ is methyl and $R_{13}$ is hydrogen.

In some embodiments, the composition the NP inhibitors have the structure of formula IV:

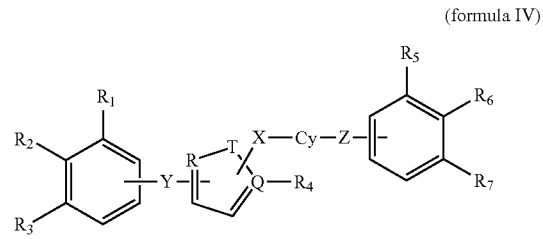

(formula IV)

wherein X, Y, and Z are independently absent or selected from the group consisting of —C(=O)—, —S(=O)—, —SO$_2$—, —N(R$_{10}$)—, —C(R$_{11}$)=C(R$_{12}$)—, and —C(R$_{13}$R$_{14}$)$_n$—;

wherein n is 0 to 6;

T, Q, and R are independently selected from C($R_8R_9$), nitrogen, oxygen, phosphorous, silicon, sulfur, and arsenic; and Cy is a 4-7-membered substituted or unsubstituted cyclic or heterocyclic group; and wherein $R_1$-$R_{14}$ are independently selected from hydrogen; halo; hydroxyl; substituted or unsubstituted, linear or branched $C_1$-$C_6$ alkyl; substituted or unsubstituted, linear or branched $C_1$-$C_6$ alkenyl; substituted or unsubstituted, linear or branched $C_1$-$C_6$ alkynyl; or substituted or unsubstituted, linear or branched $C_1$-$C_6$ alkoxy; amino; azide; cyano; nitro; nitrile; isonitrile; amide; carboxylate; urea; guanidine; isocyanate; isothiocyanate; and thioether.

In some embodiments, Cy is a substituted 5-7-membered unsaturated ring containing 2 nitrogen atoms, wherein one nitrogen atom is bonded to X and another nitrogen atom is bonded to Z.

In a preferred embodiment, Cy is a substituted piperazine, wherein N1 is bonded to X and N4 is bonded to Z, Y and Z are absent, X is C=O, T is oxygen, Q is carbon, and R is nitrogen.

In some embodiments, $R_1$-$R_3$ and $R_5$-$R_7$ are selected from a halo group, a nitro group, or a combination of a halo and nitro group.

In preferred embodiments, $R_4$ is a methyl group.

In some embodiments, the NP inhibitors have the structure of formula V:

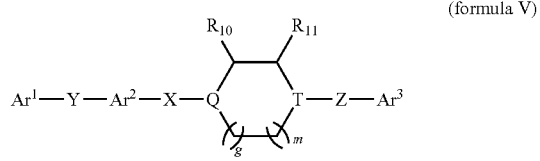

(formula V)

wherein $Ar^1$, $Ar^2$, and $Ar^3$ are each independently substituted or unsubstituted aryl or heteroaryl groups Y, and Z are independently absent or selected from the group consisting of —C=O, —S=O, —SO$_2$, —N(R$_1$)=O, —C=C, and —C(R$_2R_3$)$_n$ n, g, and m are independently 0 to 6;

Q and T are independently selected from nitrogen or $CR_4$; and $R_1$-$R_4$, $R_{10}$, and $R_{11}$ are independently selected from hydrogen; halo; hydroxyl; substituted or unsubstituted, linear or branched $C_1$-$C_6$ alkyl; substituted or unsubstituted, linear or branched $C_1$-$C_6$ alkenyl; substituted or unsubstituted, linear or branched $C_1$-$C_6$ alkynyl; or substituted or unsubstituted, linear or branched $C_1$-$C_6$ alkoxy; amino; azide; cyano; nitro; nitrile; isonitrile; amide; carboxylate; urea; guanidine; isocyanate; isothiocyanate; and thioether.

In some embodiments, Q and T are both nitrogen.

In some embodiments, $R_{10}$ is a methyl group and $R_{11}$ is hydrogen. In another embodiment, $R_{10}$ and $R_{11}$ are both hydrogen.

In some embodiments, Y and Z are absent and X is C=O.

In some embodiments, g and m are 1.

In a preferred embodiment, $Ar^1$ and $Ar^3$ are a substituted phenyl, $Ar^2$ is a substituted isoxazole, Y and Z are absent, X is C=O, Q and T are nitrogen, g and in are 1, $R_{10}$ is methyl and $R_{11}$ is hydrogen.

In some embodiments, the NP inhibitors have the structure of formula VI:

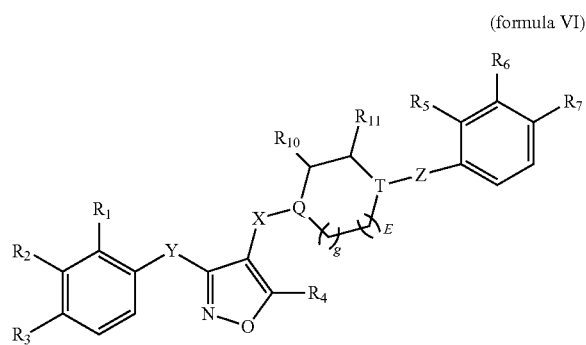

(formula VI)

wherein X, Y, and Z are independently absent or selected from the group consisting of —C(=O)—, —S(=O)—, —SO$_2$—, —N(R$_{12}$)—, —C(R$_{13}$)=C(R$_{14}$)—, and —C(R$_{15}$R$_{16}$)$_n$—, n, g, and m are independently 0 to 6;

Q and T are independently selected from nitrogen or CR$_{17}$; and $R_1$-$R_{17}$ are independently selected from hydrogen; halo; hydroxyl; substituted or unsubstituted, linear or branched $C_1$-$C_6$ alkyl; substituted or unsubstituted, linear or branched $C_1$-$C_6$ alkenyl; substituted or unsubstituted, linear or branched $C_1$-$C_6$ alkynyl; or substituted or unsubstituted, linear or branched $C_1$-$C_6$ alkoxy; amino; azide; cyano; nitro; nitrile; isonitrile; amide; carboxylate; urea; guanidine; isocyanate; isothiocyanate; and thioether.

In some embodiments, Q and T are both nitrogen.

In some embodiments, $R_{10}$ is a methyl group and $R_{11}$ is hydrogen. In other embodiments, both $R_{10}$ and $R_{11}$ are hydrogen.

In some embodiments, Y and Z are absent and X is C=O.

In some embodiments, g and m are 1.

In some embodiments, $R_1$-$R_3$ and $R_5$-$R_7$ are selected from a halo group, a nitro group, or a combination of a halo and nitro group.

The compounds can be administered to prevent and/or treat a viral infection, such as influenza. The compounds can be administered parenterally, such as in the form of a solution or suspension, or enterally, such as in the form of a tablet or capsule.

The pharmaceutical compositions contain an effective amount of one or more of the compounds described herein. The range of an effective amount may vary from individual to individual; however, the optimal dose is readily determinable by those of skill in the art, such as the prescribing physician.

Doses may be measured by total amount given (e.g. per dose or per day) or by concentration. In one embodiment, doses of 0.01, 0.05, 0.1, 0.2, 0.5, 1, 2, 3, 4, 5, 6, 7, 8, 9, 10, 15, 20, 25, 30, 40, 50, 100, 250, 500 and 1000 mg/kg/day may be appropriate for treatment. In another embodiment, the daily dosage is 0.2 to 250 mg/kg.

DETAILED DESCRIPTION OF THE INVENTION

I. Definitions

Figure 1A:
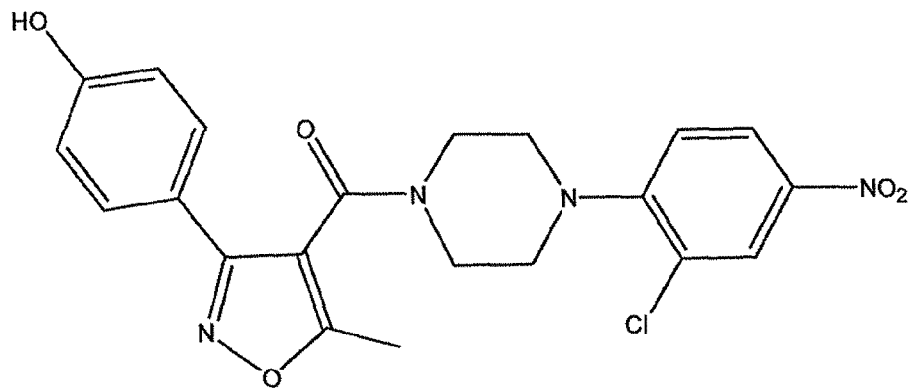
FIG. 1A is the chemical structure of Compound 1.
Figure 1B:
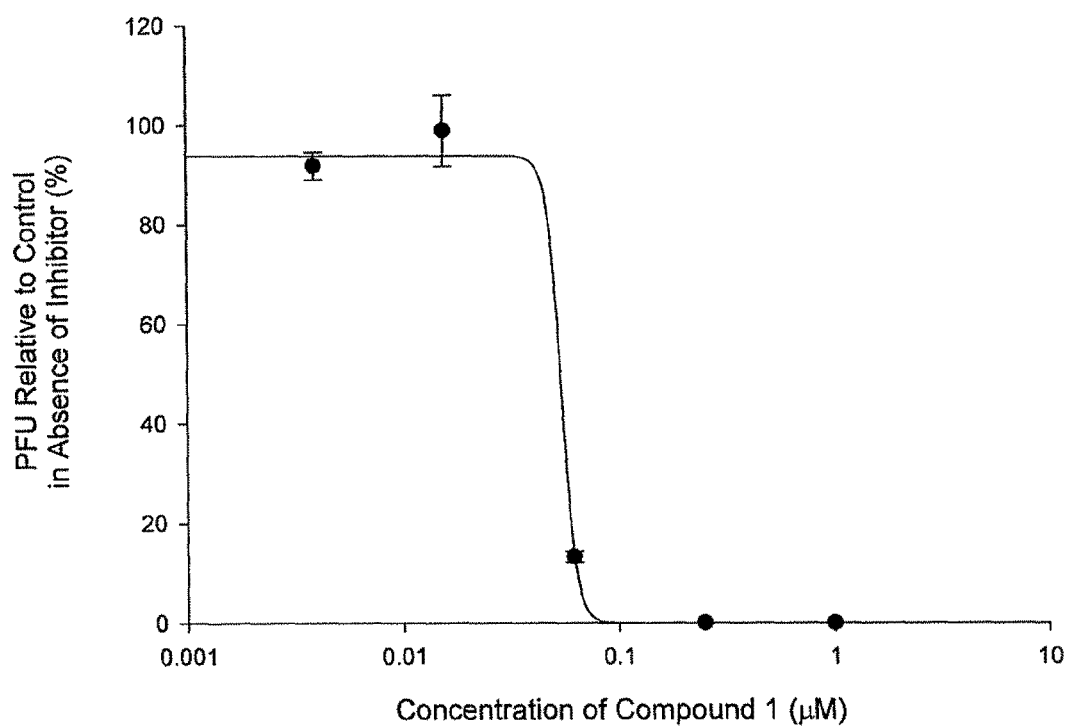
FIG. 1B is a graph showing the percent reduction in plaque forming units (PFU) as a function of the concentration of Compound 1.

"Alkyl" as generally used herein refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl generally has 30 or fewer carbon atoms in its backbone (e.g., $C_1$-$C_{30}$ for straight chain, $C_3$-$C_{30}$ for branched chain), preferably 20 or fewer, preferably 10 or fewer, more preferably 6 or fewer, most preferably 5 or fewer. If the alkyl is unsaturated, the alkyl chain generally has from 2-30 carbons in the chain, preferably from 2-20 carbons in the chain, preferably from 2-10 carbons in the chain, more preferably from 2-6 carbons, most preferably from 2-5 carbons. Likewise, preferred cycloalkyls have from 3-20 carbon atoms in their ring structure, preferably from 3-10 carbons atoms in their ring structure, most preferably 5, 6 or 7 carbons in the ring structure. Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadien yl, 3-(1,4-pentadienyl), ethynyl, 1- and 3-propynyl, and 3-butynyl.

The term "alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —$NR_1R_2$, wherein $R_1$ and $R_2$ are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —$CONR_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, —$CF_3$; —$NCOCOCH_2CH_2$; —NCOCOCHCH; —NCS; and combinations thereof.

"Aryl," as generally used herein, refers to a carbon based aromatic ring, including phenyl, biphenyl, or naphthyl. The aryl group can be optionally substituted with one or more moieties selected from the group consisting of hydroxyl, acyl, amino, halo, alkylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al. Protective Groups in Organic Synthesis, John Wiley and Sons, Third Edition, 2002. The term "aryl" includes one or more substitutions at one or more carbon atoms of the hydrocarbon radical. Suitable substituents include, but are not limited to, halogens, such as fluorine, chlorine, bromine, or iodine; hydroxyl; —$NR_1R_2$, wherein $R_1$ and $R_2$ are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —$CONR_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, —$CF_3$; —$NCOCOCH_2CH_2$; —NCOCOCHCH; —NCS; and combinations thereof.

"Binding pocket" or "binding site" as generally used herein refer to a region of a molecule or molecular complex that, as a result of its configuration, favorably associates with, or is occupied by, a moiety or region of the same molecule or molecular complex, or a moiety or region of a different molecule, molecular complex, and/or chemical compound. As will be appreciated by those of skill in the art, the nature of the cavity within a binding pocket will vary from molecule to molecule.

"Nucleozin binding site" as generally used herein refers to a site on influenza nucleoprotein (NP) A located in the body domain on the back of influenza A NP. In this conformation the nucleozin is located between residues 280 to 311 in the groove. Those skilled in the art will appreciate that the nucleozin binding site is slightly different depending on the compound bound therein and can incorporate other contacts in place of and/or in addition to the ones disclosed herein.

"Heterocycle" or "heterocyclic" as generally used herein refers to one or more rings of 5-12 atoms, preferably 5-7 atoms, with or without unsaturation or aromatic character and having at least one ring atom which is not a carbon. Preferred heteroatoms include sulfur, oxygen, and nitrogen. Multiple rings may be fused, as in quinoline or benzofuran. Particularly preferred heterocycle groups are 5-10-membered rings with 1-3 heteroatoms selected from O, S, P, Si, As, and N. Heterocycles include, but are not limited to azolidine, pyrrole, oxolane, furan, thiolane, thiophene, phospholane, phosphole, silane, silole, arsolane, arsole, imidazoline, pyrazolidine, imidazole, imidazoline, pyrazole, pyrazoline, oxazolidine, isoxazolidine, oxazole, oxazoline, isoxazole, isoxazoline, thiazolidine, isothiazolidine, thiazole, thiazoline, isothiazole, isothiazoline, dioxolane, oxathiolane, dithiolane, thiazole, dithiazole, furazan, oxadiazole, thiadiazole, tetrazole, piperidine, pyridine, pyran, tetrahydropyran, thiane, thiopyran, piperazine, diazine, morpholine, oxazine, thiazine, dithiane, dioxane, dioxin, triazine, trioxane, tetrazine, azapane, azepine, oxepane, oxepine, thiepane, thiepine, azocane, azocine, oxecane, and thiocane. Heterocycle or heterocyclic also refers to substituted rings, as defined in "aryl" or "alkyl."

The term "heterocycle" includes one or more substitutions at one or more carbon or heteroatoms. Suitable substituents include, but are not limited to, halogens, such as fluorine, chlorine, bromine, or iodine; hydroxyl; —$NR_1R_2$, wherein $R_1$ and $R_2$ are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —$CONR_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, —$CF_3$; —$NCOCOCH_2CH_2$; —NCOCOCHCH; —NCS; and combinations thereof.

"Heteroaryl" as generally used herein refers to an aromatic group containing from one to four N, O, P, Si, As, or S atoms(s) or a combination thereof, which heteroaryl group is optionally substituted at carbon or nitrogen atom(s). Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5 membered heteroaryls having two heteroatoms in 1, 2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heteroaryls with three heteroatoms (e.g., 1,3,5-triazine); and 6-membered heteroaryls with four heteroatoms. Particularly preferred heteroaryl groups are 5-10-membered rings with 1-3 heteroatoms selected from O, S, and N.

The term "heteroaryl" includes one or more substitutions at one or more carbon or heteroatoms atoms. Suitable substituents include, but are not limited to, halogens, such as fluorine, chlorine, bromine, or iodine; hydroxyl; —$NR_1R_2$, wherein $R_1$ and $R_2$ are independently hydrogen, alkyl, or aryl, and wherein the nitrogen atom is optionally quaternized; —SR, wherein R is hydrogen, alkyl, or aryl; —CN; $NO_2$; —COOH; carboxylate; —COR, —COOR, or —$CONR_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, —$CF_3$; —$NCOCOCH_2CH_2$; —NCOCOCHCH; —NCS; and combinations thereof.

"Influenza A" as generally used herein refers to mammalian Influenza A virus, e.g., H3N2, H1N1, H2N2, H7N7 and H5N1 (avian influenza virus) strains and variants thereof.

"Low energy, stable complex" as generally used herein refers to a complex in which a drug is bound in the binding site of the nucleoprotein by weak to strong intermolecular forces including, but not limited to, covalent bonds, hydrogen bonds, disulfide bonds, salt bridges, ionic bonds, metal coordination, hydrophobic forces, van der Waals interactions, cation-pi interactions, pi-stacking, and combinations thereof.

"Nucleoprotein" or "NP" as generally used herein refers to any protein that is structurally associated with nucleic acid. Exemplary nucleoproteins are identified and sequenced in certain strains of influenza viruses. The sequences of many nucleoproteins can be found in the NCBI database. The GenBank accession numbers of some exemplary NP sequences from influenza type A for subtype H1N1 are NP 040982 (AAA43467), for subtype H3N2 are AAZ38620 (YP308843); and for subtype H5N1 are AY856864 and AAF02400.

"Nucleozin" as generally referred to herein has the chemical structure as follows:

"Pharmaceutically acceptable" as generally used herein refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Pharmaceutically acceptable salts" as generally used herein refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, oxalic, and isethionic.

"Substituted" as generally used herein refers to a moiety (e.g., an alkyl group) substituted with one or more substituents including, but not limited to: alkyl, alkenyl, alkynyl, $C_3$-$C_8$ cycloalkyl, halo, e.g., fluoro, chloro, bromo, and iodo; cyano; alkoxy; hydroxy, phenyl; and substituted phenyl.

"Substituted aryl" as generally used herein refers to aryl groups having one or more non-interfering groups as a substituent. For substitutions on a phenyl ring, the substituents may be in any orientation (i.e., ortho, meta, and/or para).

II. Compounds

Compounds having antiviral activity, particularly against influenza viruses, are described herein.

In some embodiments, the compounds have the formulae I-VI below, or pharmaceutically acceptable salts thereof.

In preferred embodiments, the NP inhibitors have the structure of formula I:

$$Ar^1—Y—Ar^2—X—W—Z—Ar^3 \quad \text{(Formula I)}$$

wherein $Ar^1$, $Ar^2$, and $Ar^3$ are each independently substituted or unsubstituted aryl or heteroaryl groups;

X, Y, and Z are independently absent (i.e., a direct bond) or selected from —C(═O)—, —S(═O)—, —$SO_2$—, —$N(R_1)$—, —$C(R_2)$═$C(R_3)$—, and —$C(R_4R_5)_n$—, wherein n is 0 to 6 and wherein $R_1$-$R_5$ are each independently selected from hydrogen; hydroxyl; halogen; substituted or unsubstituted amino; —CN; —$NO_2$; —COON; carboxylate; —COR, —COOR, or —$CON(R)_2$; substituted or unsubstituted aryl, such as phenyl or benzyl; substituted or unsubstituted, linear or branched $C_1$-$C_6$ alkyl; substituted or unsubstituted, linear or branched $C_1$-$C_6$ alkenyl; substituted or unsubstituted, linear or branched $C_1$-$C_6$ alkynyl; substituted or unsubstituted $C_3$-$C_6$ cycloalkyl or cycloalkenyl; or substituted or unsubstituted, linear and branched $C_1$-$C_6$ alkoxy; and W is a linear group or a is 5-7 membered substituted or unsubstituted cyclic or heterocyclic group (Cy).

In some embodiments, $Ar^1$ is substituted with hydrogen, hydroxyl, nitro, amino, or azide; $Ar^2$ is substituted with a methyl group; X is C═O; Y and Z are absent; Cy is piperazine; and $Ar^3$ is substituted with a halo group, a nitro group, or a combination of a halo and nitro group.

In some embodiments, Cy is a substituted 5-7 membered unsaturated ring containing 2 nitrogen atoms, wherein one nitrogen atom is bonded to X and another nitrogen atom is bonded to Z.

In a preferred embodiment, Cy is a substituted piperazine, wherein N1 is bonded to X and N4 is bonded to Z.

In some embodiments, the NP inhibitors have the structure of formula II:

(formula II)

wherein $Ar^1$ and $Ar^3$ are each independently substituted or unsubstituted aryl or heteroaryl groups;

X, Y, and Z are independently absent or selected from the group consisting of —C(═O)—, —S(═O)—, —$SO_2$—, —$N(R_{10})$—, —$C(R_{11})$═$C(R_{12})$—, and —$C(R_{13}R_{14})_n$—, n, g, and m are independently 0 to 6;

T, Q, and R are independently selected from $C(R_8R_9)$, nitrogen, oxygen, phosphorous, silicon, sulfur, and arsenic;

A and D are each independently $CR_{15}R_{16}$ or $NR_{17}$;

wherein $R_4$ and $R_8$-$R_{17}$ are independently selected from hydrogen; halo; hydroxyl; substituted or unsubstituted, linear or branched $C_1$-$C_6$ alkyl; substituted or unsubstituted, linear or branched $C_1$-$C_6$ alkenyl; substituted or unsubstituted, linear or branched $C_1$-$C_6$ alkynyl; or substituted or unsubstituted, linear or branched $C_1$-$C_6$ alkoxy; amino; azide; cyano; nitro; nitrile; isonitrile; amide; carboxylate; urea; guanidine; isocyanate; isothiocyanate; and thioether, or wherein —$CR_{15}R_{16}$—, —$NR_{17}$—, or combinations thereof, when taken together with the optional bridging methylene groups, form a 5-8-membered cyclic structure.

In some embodiments, $Ar^1$ is substituted with hydrogen, hydroxyl, nitro, amino, or azide; X is —C═O; Y and Z are absent, and $Ar^3$ is substituted with a halo group, a nitro group, or a combination of a halo and nitro group.

In a preferred embodiment, $R_4$ is methyl.

In some embodiments, Q is carbon, T is oxygen, and R is nitrogen.

In some embodiments, g and m are 1 and A and D are $NR_{17}$, wherein A-D defines a piperazine.

In some embodiments, the NP inhibitors have the structure of formula III:

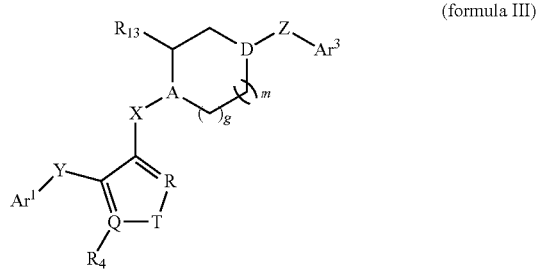

(formula III)

wherein $Ar^1$ and $Ar^3$ are each independently substituted or unsubstituted aryl or heteroaryl groups;

X, Y, and Z are independently absent or selected from the group consisting of —C(═O)—, —S(═O)—, —$SO_2$—, —$C(R_{10})$—, —$C(R_{11})$═$C(R_{12})$—, and —$C(R_{14}R_{15})_n$—, n, g, and m are independently 0 to 6;

A, D, T, Q, and R are independently selected from $C(R_5R_9)$, nitrogen, oxygen, phosphorous, sulfur, silicon, and arsenic;

wherein $R_4$ and $R_8$-$R_{15}$ are independently selected from hydrogen; halo; hydroxyl; substituted or unsubstituted, linear or branched $C_1$-$C_6$ alkyl; substituted or unsubstituted, linear or branched $C_1$-$C_6$ alkenyl; substituted or unsubstituted, linear or branched $C_1$-$C_6$ alkynyl; or substituted or unsubstituted, linear or branched $C_1$-$C_6$ alkoxy; amino; azide; cyano; nitro; nitrile; isonitrile; amide; carboxylate; urea; guanidine; isocyanate; isothiocyanate; and thioether.

In some embodiments, $Ar^1$ is substituted with hydrogen, hydroxyl, nitro, amino, or azide; X is C═O; Y and Z are absent, and $Ar^3$ is substituted with a halo group, a nitro group, or a combination of a halo and nitro group.

In a preferred embodiment, Q is carbon, T is oxygen, and R is nitrogen.

In some embodiments, A and D are nitrogen.

In some embodiments, $R_4$ and $R_{13}$ are independently hydrogen or methyl. In preferred embodiments, $R_4$ is methyl and $R_{13}$ is hydrogen.

In some embodiments, the composition the NP inhibitors have the structure of formula IV:

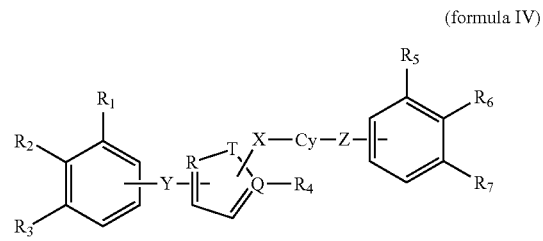

(formula IV)

wherein X, Y, and Z are independently absent or selected from the group consisting of —C(═O)—, —S(═O)—, —$SO_2$—, —$N(R_{10})$—, —$C(R_{11})$═$C(R_{12})$—, and —$C(R_{13}R_{14})_n$—;

wherein n is 0 to 6;

T, Q, and R are independently selected from $C(R_8R_9)$, nitrogen, oxygen, phosphorous, silicon, sulfur, and arsenic; and Cy is a 4-7 membered substituted or unsubstituted cyclic or heterocyclic group; and wherein $R_1$-$R_{14}$ are independently selected from hydrogen; halo; hydroxyl; substituted or unsubstituted, linear or branched $C_1$-$C_6$ alkyl; substituted or unsubstituted, linear or branched $C_1$-$C_6$ alkenyl; substituted or unsubstituted, linear or branched $C_1$-$C_6$ alkynyl; or substituted or unsubstituted, linear or branched $C_1$-$C_6$ alkoxy; amino; azide; cyano; nitro; nitrile; isonitrile; amide; carboxylate; urea; guanidine; isocyanate; isothiocyanate; and thioether.

In some embodiments, Cy is a substituted 5-7 membered unsaturated ring containing 2 nitrogen atoms, wherein one nitrogen atom is bonded to X and another nitrogen atom is bonded to Z.

In a preferred embodiment, Cy is a substituted piperazine, wherein N1 is bonded to X and N4 is bonded to Z, Y and Z are absent, X is C═O, T is oxygen, Q is carbon, and R is nitrogen.

In some embodiments, $R_1$-$R_3$ and $R_5$-$R_7$ are selected from a halo group, a nitro group, or a combination of a halo and nitro group.

In preferred embodiments, $R_4$ is a methyl group.

In some embodiments, the NP inhibitors have the structure of formula V:

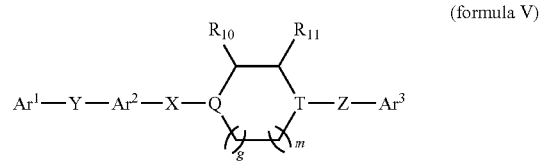

(formula V)

wherein $Ar^1$, $Ar^2$, and $Ar^3$ are each independently substituted or unsubstituted aryl or heteroaryl groups X, Y, and Z are independently absent or selected from the group consisting of —C═O, —S═O, —$SO_2$, —$N(R_1)$═O, —C═C, and —$C(R_2R_3)_n$ n, g, and m are independently 0 to 6;

Q and T are independently selected from nitrogen or $CR_4$; and $R_1$-$R_4$, $R_{10}$, and $R_{11}$ are independently selected from hydrogen; halo; hydroxyl; substituted or unsubstituted, linear or branched $C_1$-$C_6$ alkyl; substituted or unsubstituted, linear or branched $C_1$-$C_6$ alkenyl; substituted or unsubstituted, linear or branched $C_1$-$C_6$ alkynyl; or substituted or unsubstituted, linear or branched $C_1$-$C_6$ alkoxy; amino; azide; cyano; nitro; nitrile; isonitrile; amide; carboxylate; urea; guanidine; isocyanate; isothiocyanate; and thioether.

In some embodiments, Q and T are both nitrogen.

In some embodiments, $R_{10}$ is a methyl group and $R_{11}$ is hydrogen. In another embodiment, $R_{10}$ and $R_{11}$ are both hydrogen.

In some embodiments, Y and Z are absent and X is C=O.

In some embodiments, g and m are 1.

In a preferred embodiment, $Ar^1$ and $Ar^3$ are a substituted phenyl, $Ar^2$ is a substituted isoxazole, Y and Z are absent, X is C=O, Q and T are nitrogen, g and m are 1, $R_{10}$ is methyl and $R_{11}$ is hydrogen.

In some embodiments, the NP inhibitors have the structure of formula VI:

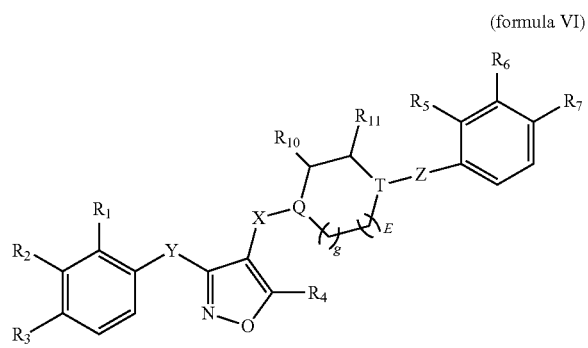

(formula VI)

wherein X, Y, and Z are independently absent or selected from the group consisting of —C(=O)—, —$SO_2$—, —S(=O)—, —N($R_{12}$)—, —C($R_{13}$)=C($R_{14}$)—, and —C($R_{15}R_{16}$)$_n$—, n, g, and m are independently 0 to 6;

Q and T are independently selected from nitrogen or $CR_{17}$; and $R_1$-$R_{17}$ are independently selected from hydrogen; halo; hydroxyl; substituted or unsubstituted, linear or branched $C_1$-$C_6$ alkyl; substituted or unsubstituted, linear or branched $C_1$-$C_6$ alkenyl; substituted or unsubstituted, linear or branched $C_1$-$C_6$ alkynyl; or substituted or unsubstituted, linear or branched $C_1$-$C_6$ alkoxy; amino; azide; cyano; nitro; nitrile; isonitrile; amide; carboxylate; urea; guanidine; isocyanate; isothiocyanate; and thioether.

In some embodiments, Q and T are both nitrogen.

In some embodiments, $R_{10}$ is a methyl group and $R_{11}$ is hydrogen. In other embodiments, both $R_{10}$ and $R_{11}$ are hydrogen.

In some embodiments, Y and Z are absent and X is C=O.

In some embodiments, g and m are 1.

In some embodiments, $R_1$-$R_3$ and $R_5$-$R_7$ are selected from a halo group, a nitro group, or a combination of a halo and nitro group.

In preferred embodiments, $R_4$ is a methyl group.

Figure 2A:
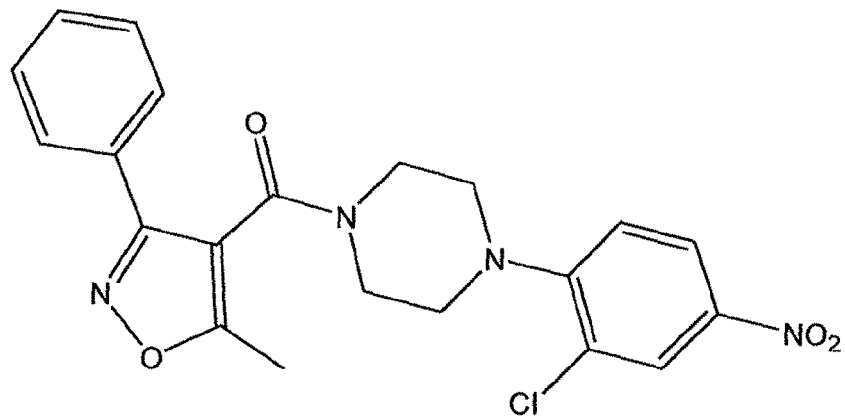
FIG. 2A is the chemical structure of Compound 2.
Figure 2B:
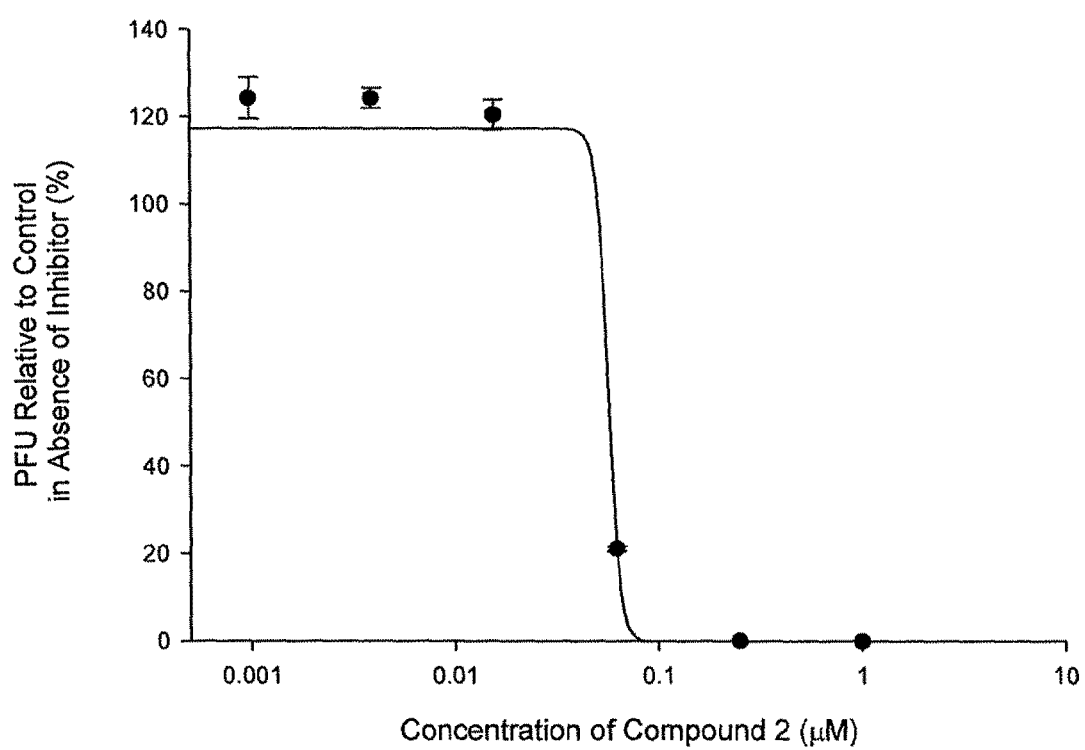
FIG. 2B is a graph showing the percent reduction in plaque forming units (PFU) as a function of the concentration of Compound 2.
Figure 3A:
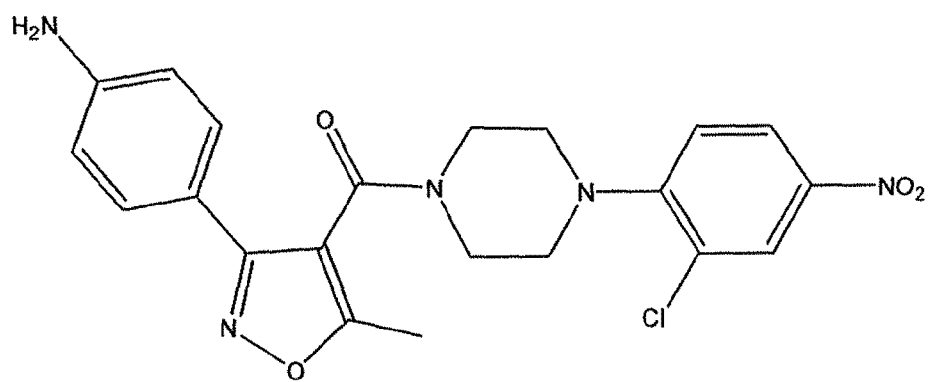
FIG. 3A is the chemical structure of Compound 3.
Figure 3B:
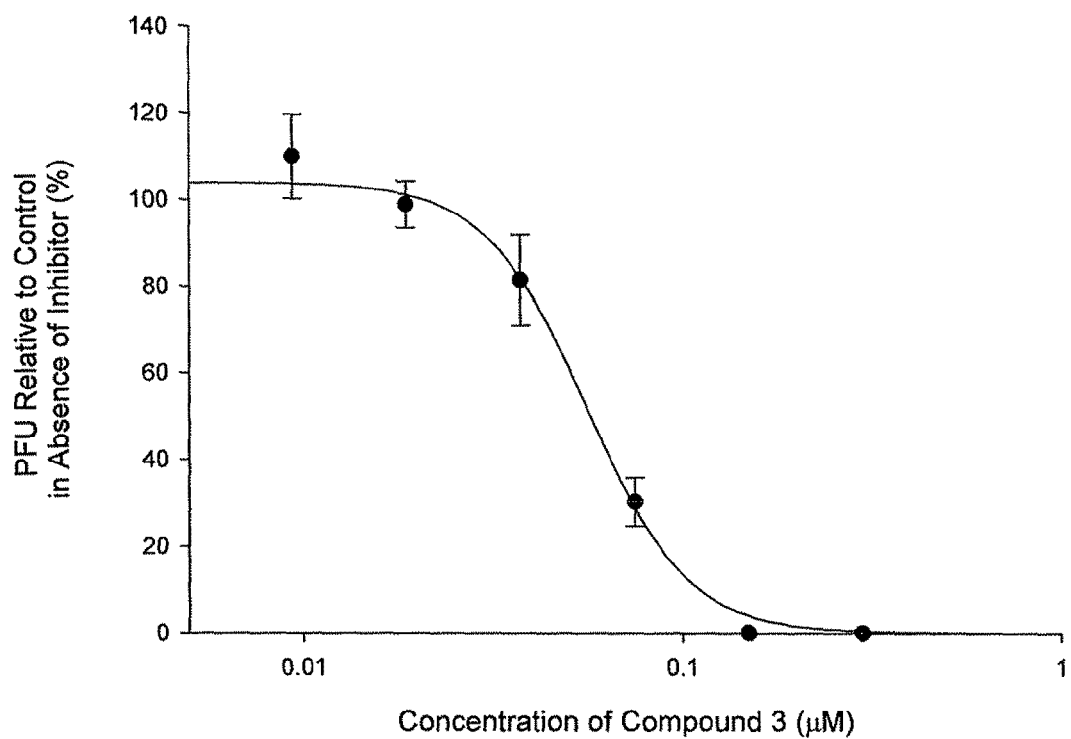
FIG. 3B is a graph showing the percent reduction in plaque forming units (PFU) as a function of the concentration of Compound 3.
Figure 4A:
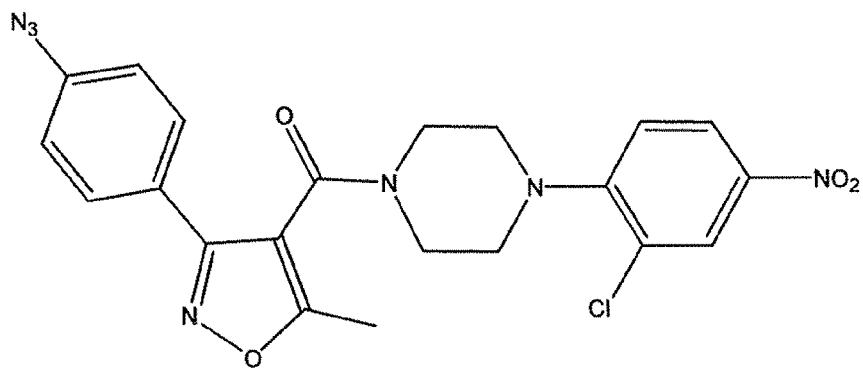
FIG. 4A is the chemical structure of Compound 4.
Figure 4B:
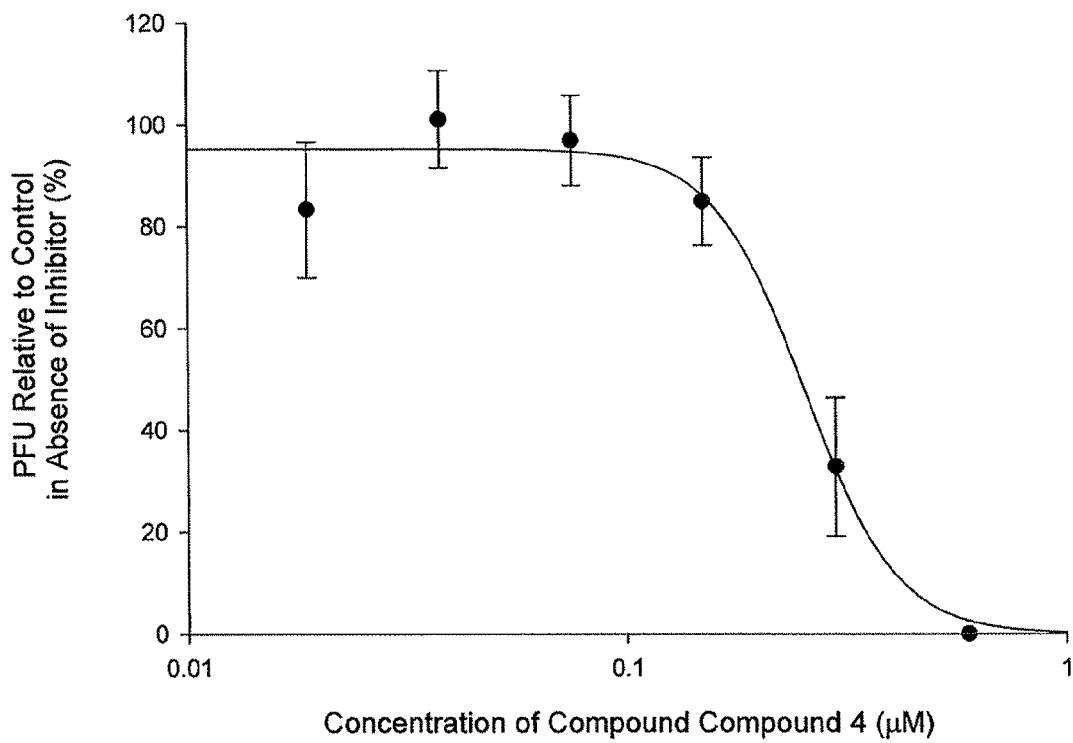
FIG. 4B is a graph showing the percent reduction in plaque forming units (PFU) as a function of the concentration of Compound 4.
Figure 5A:
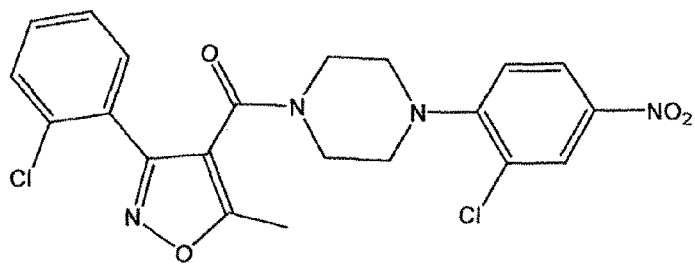
FIG. 5A is the chemical structure of Compound 5.
Figure 5B:
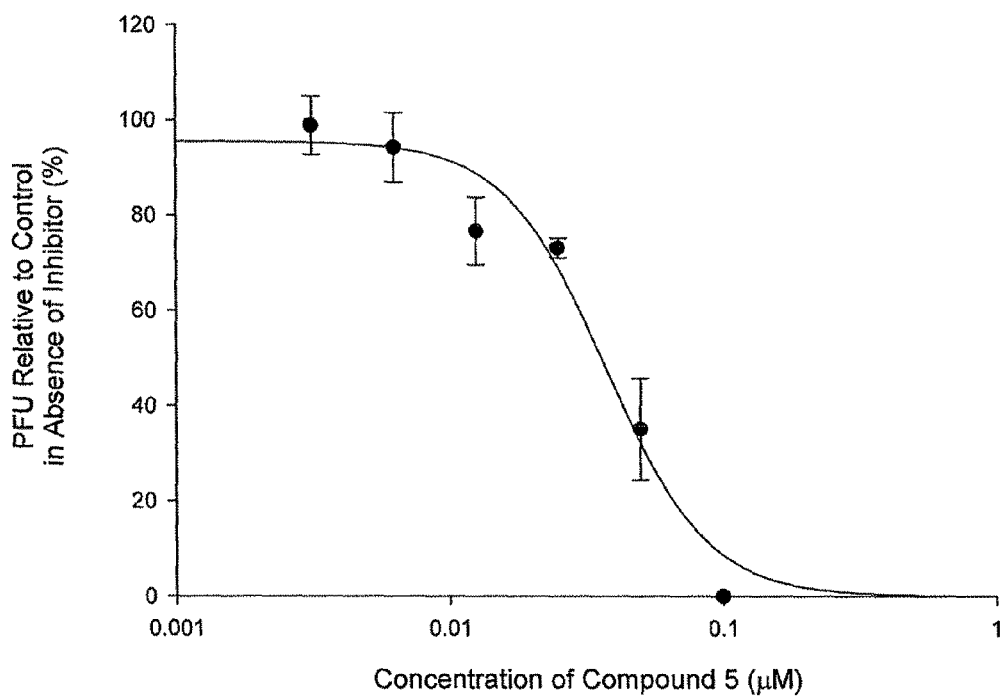
FIG. 5B is a graph showing the percent reduction in plaque forming units (PFU) as a function of the concentration of Compound 5.
Figure 6A:
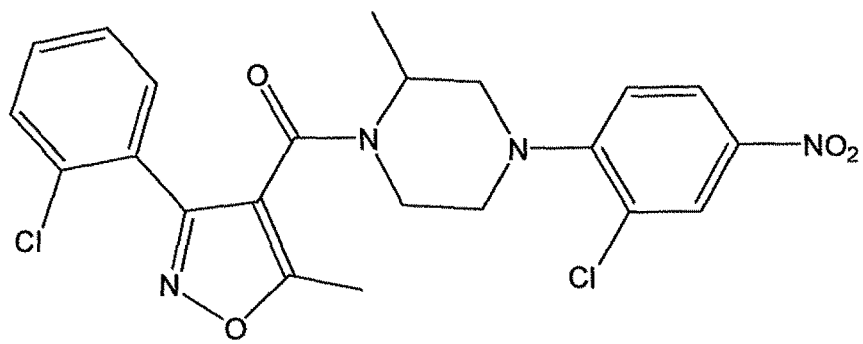
FIG. 6A is the chemical structure of Compound 6.
Figure 6B:
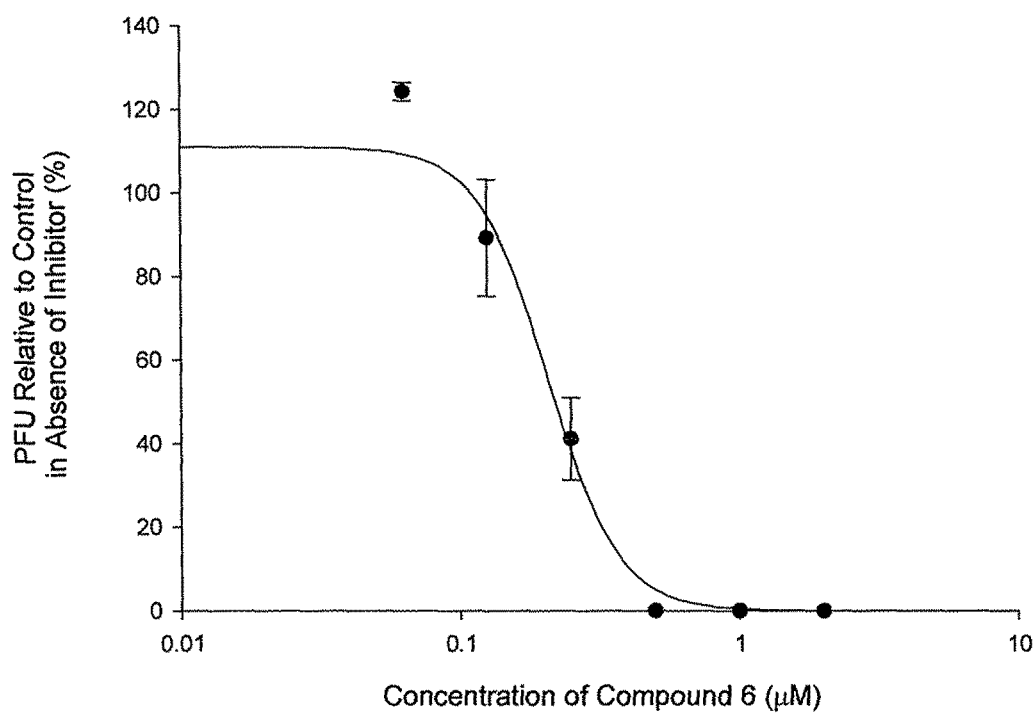
FIG. 6B is a graph showing the percent reduction in plaque forming units (PFU) as a function of the concentration of Compound 6.
Figure 7A:
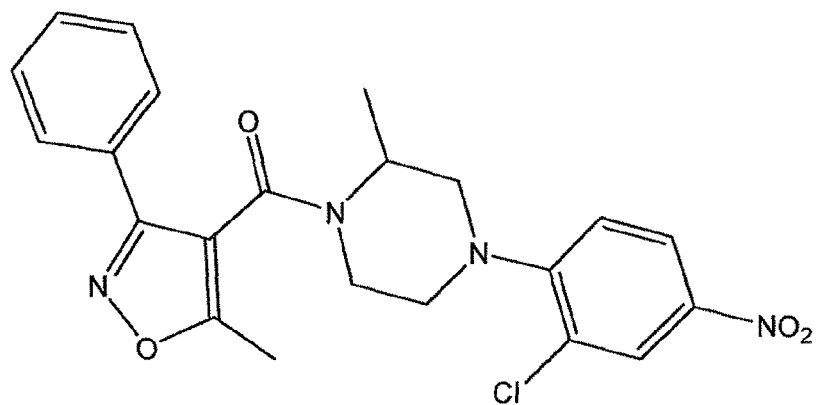
FIG. 7A is the chemical structure of Compound 7.
Figure 7B:
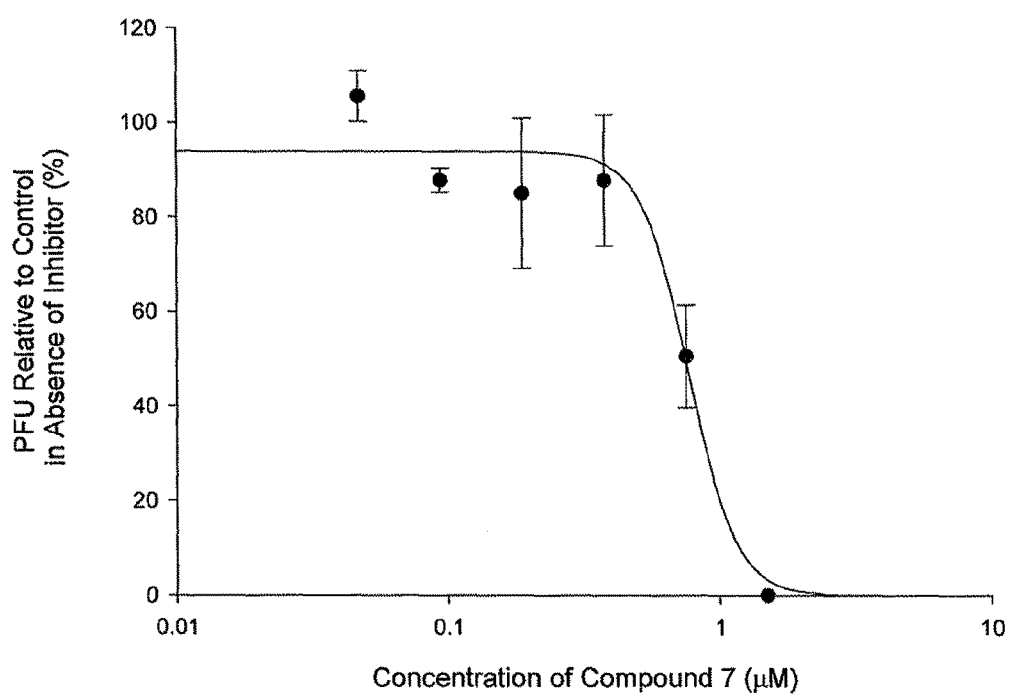
FIG. 7B is a graph showing the percent reduction in plaque forming units (PFU) as a function of the concentration of Compound 7.
Figure 8A:
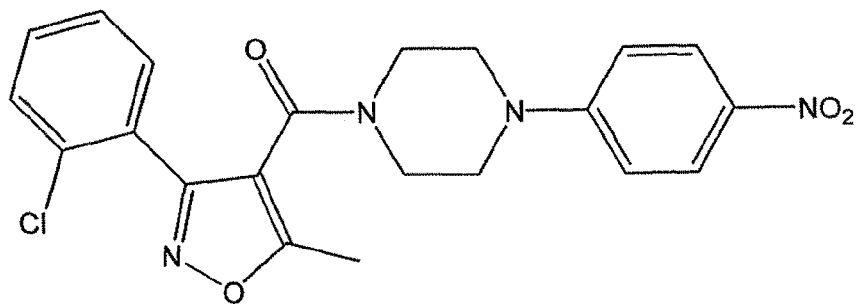
FIG. 8A is the chemical structure of Compound 8.
Figure 8B:
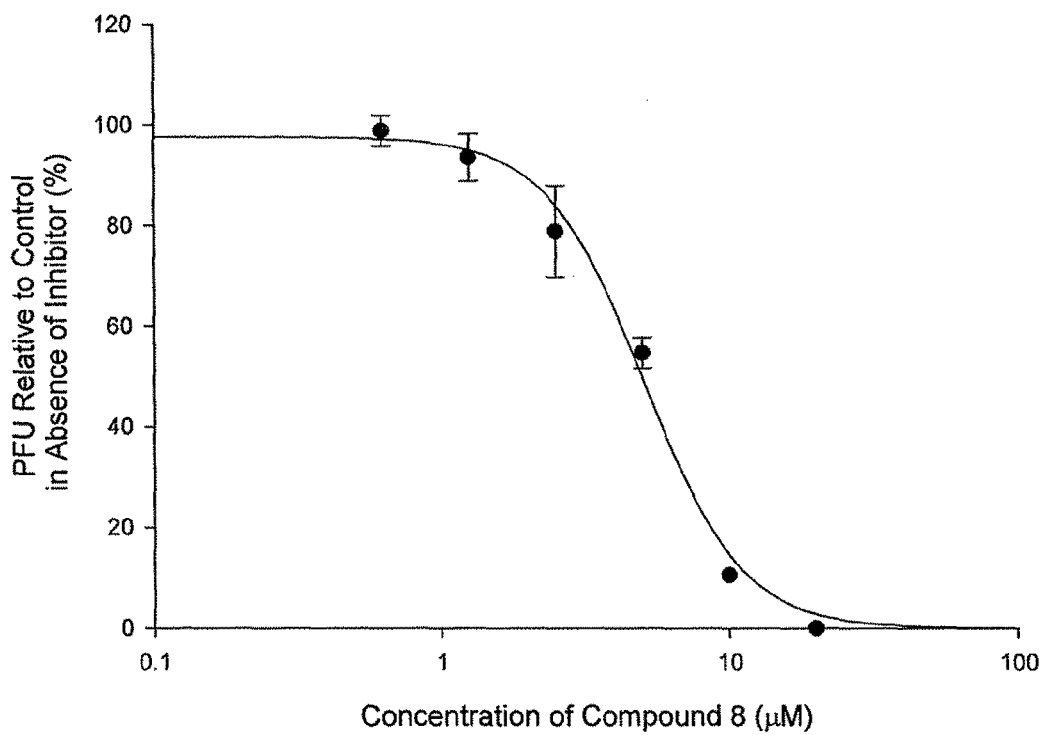
FIG. 8B is a graph showing the percent reduction in plaque forming units (PFU) as a function of the concentration of Compound 8.
Figure 9A:
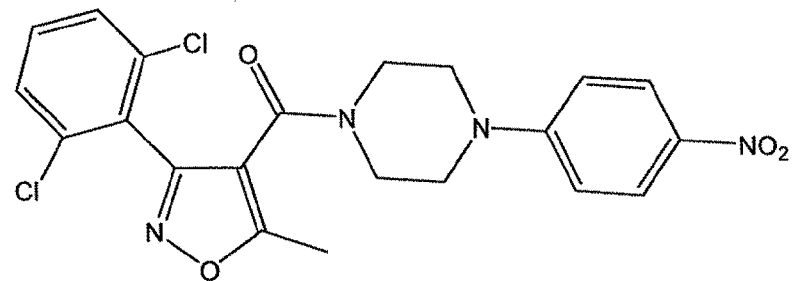
FIG. 9A is the chemical structure of Compound 9.
Figure 9B:
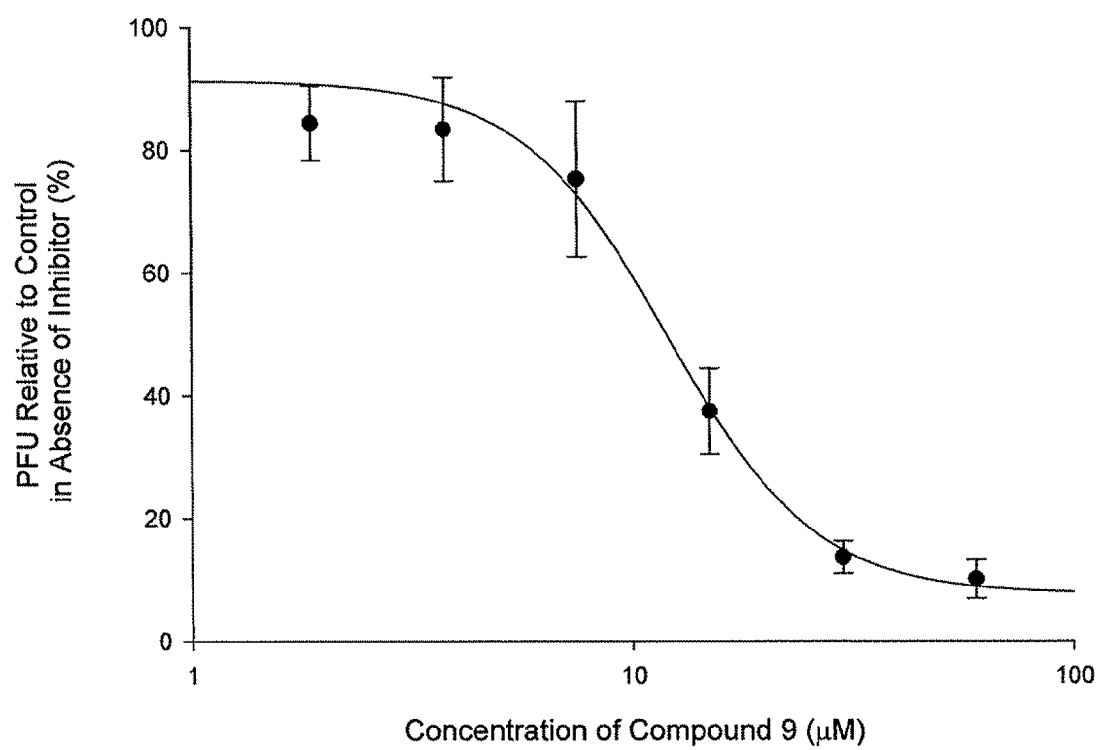
FIG. 9B is a graph showing the percent reduction in plaque forming units (PFU) as a function of the concentration of Compound 9.

Exemplary referred compounds described herein are:

[4-(2-chloro-4-nitro-phenyl)-piperazin-1-yl]-[3-(4-hydroxy-phenyl)-5-methylisoxazol-4-yl]-methanone (Compound 1, structural formula show in FIG. 1a);

[4-(2-chloro-4-nitro-phenyl)-piperazin-1-yl]-[3-phenyl-5-methyl-isoxazol-4-yl]-methanone (Compound 2, structural formula show in FIG. 2a);

[4-(2-chloro-4-nitro-phenyl)-piperazin-1-yl]-[3-(4-aminophenyl)-methylisoxazol-4-yl]-methanone (Compound 3, structural formula show in FIG. 3a);

[4-(2-chloro-4-nitro-phenyl)-piperazin-1-yl]-[3-(4-azido-phenyl)-5-methylisoxazol-4-yl]-methanone (Compound 4, structural formula show in FIG. 4a);

[4-(2-chloro-4-nitro-phenyl)-piperazin-1-yl]-[3-(2-chloro-phenyl)-5-methylisoxazol-4-yl]-methanone (Compound 5, structural formula show in FIG. 5a);

[4-(2-chloro-4-nitro-phenyl)-2-methyl-piperazin-1-yl]-[3-(2-chloro-phenyl)-5-methyl-isoxazol-4-yl]-methanone (Compound 6, structural formula show in FIG. 6a);

[4-(2-chloro-4-nitro-phenyl)-2-methyl-piperazin-1-yl]-[3-phenyl-5-methylisoxazol-4-yl]-methanone (Compound 7, structural formula show in FIG. 7a);

[4-(4-nitro-phenyl)-piperazin-1-yl]-[3-(2-chloro-phenyl)-5-methyl-isoxazol-4-yl]-methanone (Compound 8, structural formula show in FIG. 8a);

and [4-(4-nitro-phenyl)-piperazin-1-yl]-[3-(2,6-dichloro-phenyl)-5-methyl-isoxazol-4-yl]-methanone (Compound 9, structural formula show in FIG. 9a).

Figure 10A:
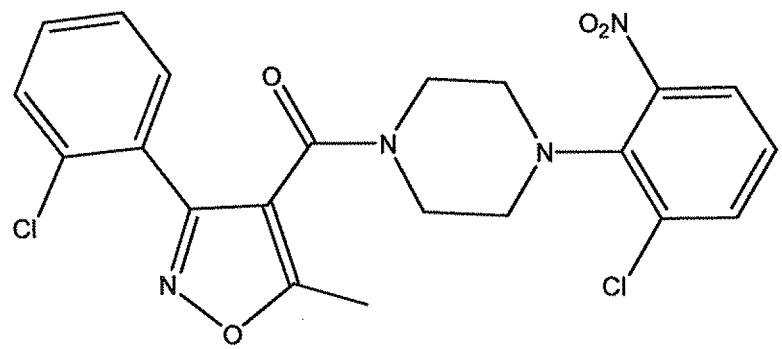
FIG. 10A is the chemical structure of Compound 10.
Figure 10B:
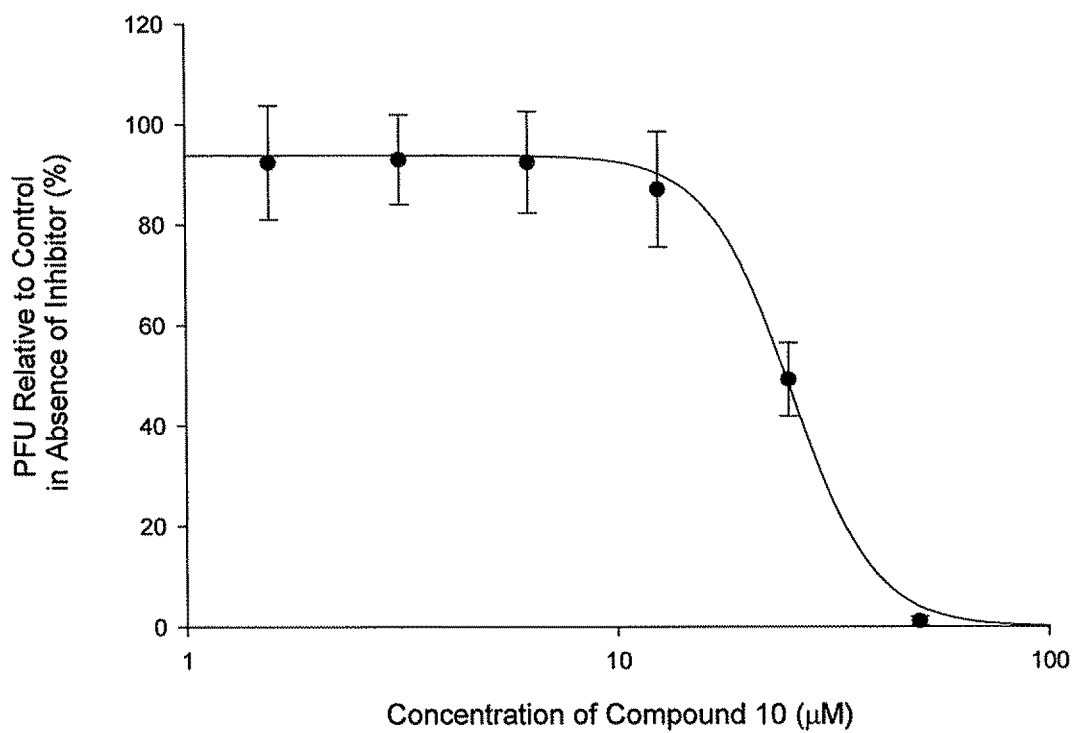
FIG. 10B is a graph showing the percent reduction in plaque forming units (PFU) as a function of the concentration of Compound 10.

[4-(2-nitro-6-chloro-phenyl)-piperazin-1-yl]-[3-(2-chloro-phenyl)-5-methyl-isoxazol-4-yl]-methanone (Compound 10, structural formula shown in FIG. 10a).

The compounds described herein can be administered as the free acid or free base or as a pharmaceutically acceptable salt. The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704.

B. Pharmaceutical Compositions

The compounds described herein, and/or their pharmaceutically acceptable salts, can be formulated into dosage forms suitable for enteral and parenteral administration using techniques known in the art.

The pharmaceutical compositions contain an effective amount of one or more of the compounds described herein. "Effective amount" as generally used herein refers to an amount, or dose, within the range normally given or prescribed to demonstrate an anti-viral effect, e.g., in vitro or in vivo. The range of an effective amount may vary from individual to individual; however, the optimal dose is readily determinable by those of skill in the art, such as the prescribing physician. Such ranges are well established in routine clinical practice and will thus be readily determinable to those of skill in the art. Doses may be measured by total amount given (e.g. per dose or per day) or by concentration. Doses of 0.01, 0.05, 0.1, 0.2, 0.5, 1, 2, 3, 4, 5, 6, 7, 8, 9, 10, 15, 20, 25, 30, 40, 50, 100, 250, 500 and 1000 mg/kg/day may be appropriate for treatment. In one embodiment, the daily dosage is 0.2 to 250 mg/kg.

The compounds described herein can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients.

1. Parenteral Formulations

The compounds described herein can be formulated for parenteral administration. "Parenteral administration", as used herein, means administration by any method other than through the digestive tract or non-invasive topical or regional routes. For example, parenteral administration may include administration to a patient intravenously, intradermally, intraperitoneally, intrapleurally, intratracheally, intramuscularly, subcutaneously, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection, such as micro- or nanoparticles; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersions and/or by the use of surfactants. In many cases, it will be preferable to include isotonic agents, for example, sugars or salts, such as sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-D-alanine, sodium N-lauryl-☐-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The composition is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

The parenteral formulations described herein can be formulated for controlled release including immediate release, delayed release, extended release, pulsatile release, and combinations thereof.

For parenteral administration, the one or more NP inhibitors, and optional one or more additional active agents, can be incorporated into microparticles, nanoparticles, or combinations thereof that provide controlled release. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropylcellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins which are water insoluble, such as zein, can also be used as materials for the formation of drug containing microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. Detailed descriptions of these processes can be found in "Remington—The science and practice of pharmacy", 20th Edition, Jennaro et. al., (Phila, Lippencott, Williams, and Wilkens, 2000).

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (glutaraldehyde and formaldehyde), epoxy compounds, carbodiimides, and genipin. In addition to these cross-linking agents, oxidized and native sugars have been used to cross-link gelatin (Cortesi, R., et al., Biomaterials 19 (1998) 1641-1649). Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

2. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition which may include plasticizers, pigments, colorants, stabilizing agents, and glidants. Delayed release dosage formulations may be prepared as described in standard references such as "Pharmaceutical dosage form tablets", eds. Libeinian et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid) (anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm. Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

3. Other Active Agents

The anti-viral agents described herein can be co-administered with one or more additional active agents. "Co-administered" as used herein include administration within the same dosage form or within different dosage forms. For those embodiments where the antiviral agents described herein and the one or more additional active agents are administered in different dosage forms, the dosage forms can be administered simultaneously (e.g., at the same time or essentially at the same time) or sequentially. "Essentially at the same time" as used herein generally means within ten minutes, preferably within five minutes, more preferably within two minutes, most preferably within in one minute. Dosage forms administered sequentially can be administered within several hours of each other, e.g., with ten hours, nine hours, eight hours, seven hours, six hours, five hours, four hours, three hours, two hours, one hour, 30 minutes, 20 minutes, or 15 minutes.

The antiviral agents described herein can be administered with any class or classes of active agents known in the art. Suitable classes of compounds include, but are not limited to, other classes of antiviral agents, anti-inflammatories, cytochrome-P450 inhibitors, analgesics, anthistamines, decongestants, anti-nausea agents, agents to treat diarrhea, and combinations thereof.

III. Methods of Making the Compounds

Examples of synthesis of the compounds described herein are shown in attached Schemes 1-3. In each case, the starting materials are a 1,2-dichloro-4-nitrobenzene and piperazine, which are reacted to form the 1-(4-nitro-1-chlorophenyl)piperazine appropriate for preparing the compounds described herein.

The substituents on the benzene reagent can be varied appropriately in accordance with the end product to be prepared. The substituted piperazine so formed is reacted with a 3-phenyl-4-carboxy-isoxazole compound, appropriately substituted in accordance with the end product to be formed. The 3-phenyl-4-carboxy-isoxazole compound can be prepared from protected 1,4-dihydroxy benzene by reaction with hydroxylamine hydrochloride followed by the illustrated chemical reaction steps in Schemes 1-3. Procedures for preparing Compounds 1-10 are described in the Examples.

Scheme 1. Synthesis of Compound 1 (YD-04)

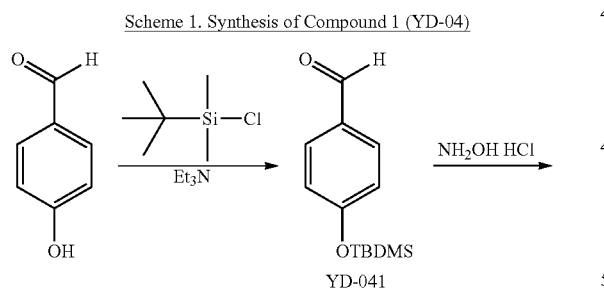

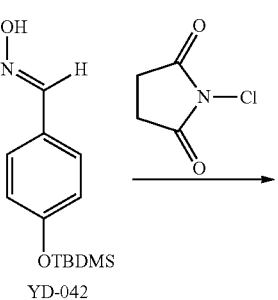

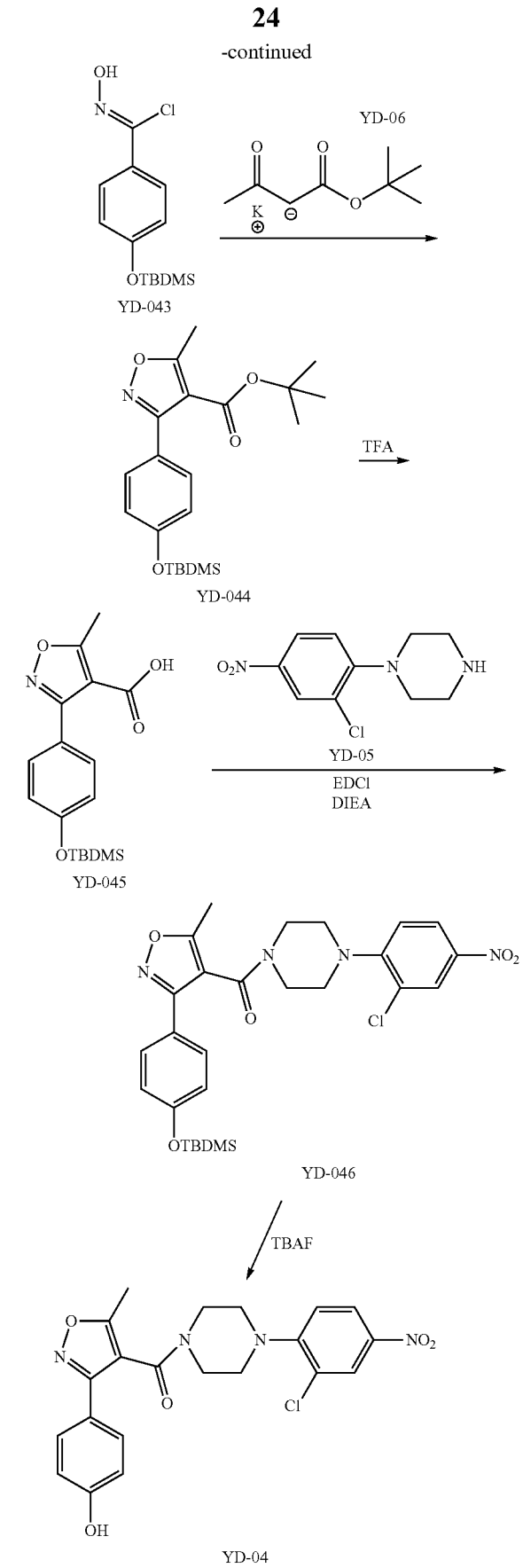

Scheme 2. The synthesis of compound 2 (YD-01):
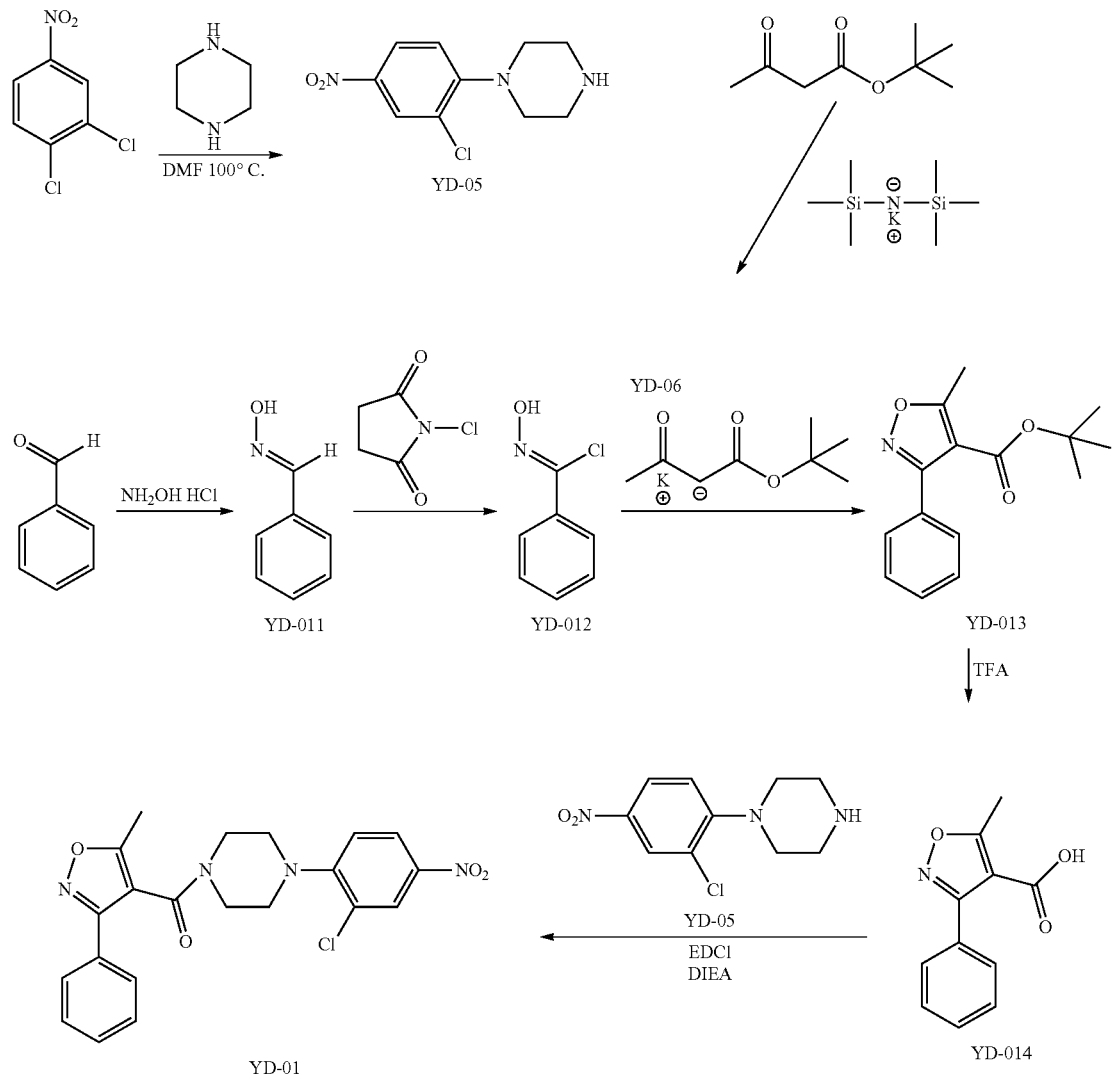
Scheme 3. Synthesis of Compound 3 (YD-03) and Compound 4 (YD-07)
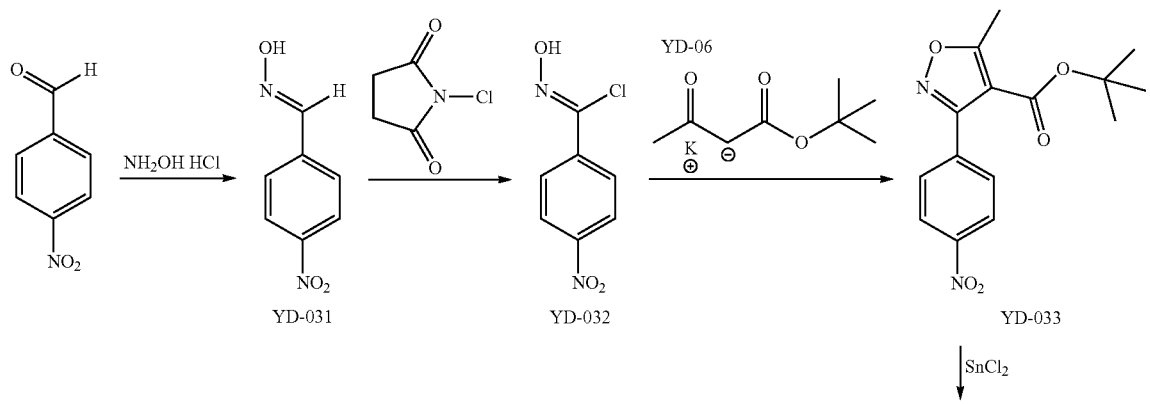

IV. Methods of Use

The anti-viral agents described herein may be used to reduce virus growth, infectivity, burden, shed, development of anti-viral resistance, and/or to enhance the efficacy of traditional anti-viral therapies.

All viruses with negative-sense RNA genomes encode a single-strand RNA-binding nucleoprotein (NP). Nucleoproteins are proteins that are structurally associated with nucleic acid (either DNA or RNA). Influenza nucleoprotein is the most abundantly expressed protein during the course of infection with multiple functions including shuttling between the nucleus and the cytoplasm and encapsidation of the virus genome for RNA transcription, replication and packaging. NP interacts with a wide variety of both viral and host cellular macromolecules, including itself, RNA, the viral RNA-dependent RNA polymerase, and the viral matrix protein. NP also interacts with host polypeptides (such as actin), components of the nuclear import and export apparatus, and a nuclear RNA helicase. The three potential binding novel binding sites on the influenza A NP include the small groove, the RNA binding pocket groove, and the tail loop groove.

Without being bound by any particular theory, it is hypothesized that the mechanism of action of the compounds described herein involves binding to the nucleoprotein (NP) of the virus, such as the influenza virus, to interfere with the replication of the virus in vivo.

In one embodiment, the anti-viral agents described herein bind to the small groove (called the nucleozin binding groove) in the back of the body of influenza A nucleoprotein and involves residues 280 to 311 (VYGSAVASGYDFER-EGYSLVGIDPFRLLQNSQ) (SEQ ID NO:1). The secondary structure of these residues include three short helices (280~287, 291~294, and 301~309) which are connected by loops formed by residues between helices.

The NP inhibitor can be located in a small groove on the back of the body and can interact with residue N309 by hydrogen bonding and Y289 by hydrophobic interactions, where the phenyl ring of compound may be parallel with the phenyl ring of Y289, and the distance between these two rings is between ~3.2-4.3 Å.

In a particular embodiment, the NP inhibitor binds in the small groove, and the compound forms hydrogen bonds with residue 5287. In some embodiments, the anti-viral agents can make binding contacts, alone or in combination with the above-listed contacts. In particular, anti-viral compounds can make contact with residues 465~470 (sequence: ELSDEK) (SEQ ID NO:2), residues 22~26 (sequence: ATEIR) (SEQ ID NO:3), residues A22~47L (sequence: ATEIRASVGKMID-GIGRFYIQMCTEL) (SEQ ID NO:4), R55, or combinations thereof.

In another embodiment, NP inhibitors bind to the RNA binding groove of the influenza A nucleoprotein. In this embodiment, the NP inhibitor is located in the RNA binding domain, which spans the interior groove between body and head of the nucleoprotein, and forms hydrogen bonds with residues Q364 and V363 that prohibit RNA from entering the arginine rich groove. Y148 was considered to be function as fixation of the first base of RNA.

In another embodiment, exemplary NP inhibitors bind to the tail loop groove of the influenza. In this embodiment, NP inhibitors are located in tail loop binding domain near to residue E339, and form hydrogen bonds with residues V186, R267, and G268. NP inhibitors in this binding pocket break the salt bridge formed between E339 and R416 from another monomer.

B. Disorders to be Treated

Viral infections caused by both enveloped and non-enveloped viruses, including those that infect animals, vertebrates, mammals, and human patients can be prevented or treated with the compounds or compositions described herein. The compounds are suitable for treating all viruses that infect vertebrates, particularly humans, and particularly viruses that are pathogenic in animals and humans. The viral infections and associated resultant diseases that can be treated include, but are not limited to CMV, RSV, arenavirus and HIV infections, and the diseases hepatitis, influenza, pneumonia, Lassa fever and AIDS. The International Committee on Taxonomy of Viruses contains a complete listing of viral strains known in the art and is incorporated herein by reference in its entirety.

In some embodiments, the diseases to prevent or treat include viral infections. In preferred embodiments, the compounds and formulations are used to treat or prevent influenza A viral infections. Influenza A viruses that can be prevented or treated with formulations of the present method include H1N1, H2N2, H3N2, H5N1, H7N7, H1N2, H9N2, H7N2, H7N3, and H10N7. In preferred embodiments, the present formulations are useful for treatment of the influenza infection A strain caused by H1N1 or H3N2.

C. Dosages

The dosage of an anti-viral formulation necessary to prevent viral growth and proliferation depends upon a number of factors including the types of virus that might be present, the environment into which the formulation is being introduced, and the time that the formulation is envisioned to remain in a given area.

Preferred compounds are those identified by a virtual screen. Exemplary compounds belong to formulae I-VI. Typical doses for treatment of viral infections are from about 0.1 mg to 250 mg/kg/day, preferably from 0.2 to 250 mg/kg/day.

The compounds can be administered to humans for the treatment of viral infection by either the oral or parenteral routes and may be administered orally at dosage levels of about 0.1 to about 500 mg/kg, preferably from about 0.5 to 250 mg/kg/day given once or twice a day.

Variations in dosage and formulation will result based on the weight and condition of the subject being treated and the particular route of administration chosen as will be known to those skilled in the art.

EXAMPLES

Materials and Methods

Viruses

Influenza A\WSN\33 viruses were propagated in Madin-Darby canine kidney (MDCK) cells. After full cytopathic effects were developed in infected MDCK cell cultures, the viral particles were harvested and stored in a −70° C. freezer till use. The influenza A virus strain A/Vietnam/1194/04 was grown in embryonated eggs, and the harvested virus-containing allantoic fluid was stored in aliquots at −70° C. until use.

Plaque Reduction Assay

Protective effects of the compounds were determined on MDCK cells against Influenza A H1N1\WSN\33 using plaque reduction assay.

The PRA assay was performed in triplicate in a 24-well tissue culture plates. MDCK cells were seeded at $1 \times 10^5$ cells/well using Eagle's minimal essential medium (EMEM) with 10% fetal bovine serum (FBS) one day prior to addition of the virus. After 16 to 24 hours, 100 to 200 plaque forming units (PFU) of influenza A/WSN/33 virus were added to the cell monolayer with or without the compounds. The concentration of each of compounds 1-10 was varied in the different experiments. The virus was allowed to infect the cells for 1.5 to 2 hours at 37° C. with 5% $CO_2$ before removal of unbound viral particles by aspiration. The cell monolayer was washed once with EMEM and overlaid with 1% low melting agarose in EMEM containing 1% FBS and 1 µg/ml TPCK trypsin. Compounds were also present in the agarose overlay when needed.

The plates were incubated at 37° C. with 5% $CO_2$ for 72 hours. At 72 hours post-infection, the cells were fixed with 10% formaldehyde for 3 hours and the plates were submerged in 1% Virkon disinfectant for 5 minutes. The agarose plugs were then removed and the cell monolayer was stained with 0.7% crystal violet. The plaques formed by viral infection were counted. The percentage of plaque inhibition relative to the controls (without the addition of compounds) was determined for each compound concentration. A plot was made, for each compound, of plaque formation units (PFU) relative to control in the absence of inhibitor (% reduction in PFU) as a function of the concentration of test compound. The median effective concentration, $EC_{50}$, which represents the concentration of a drug that is required to reduce the viral PFU by 50%, was calculated from the plotted graphs. Results are expressed as percentage of controls in the absence of compounds and are shown in the figures. The mean value is shown with standard deviation.

Cytotoxicity Assay

Cytotoxicity of Compounds 1-10 was measured by the 3-(4,5-dimethylthiazol-2-yl)-2,5-diphenyltetrazolium bromide (MTT, Sigma-Aldrich, USA) assay. The assay was performed by seeding Vero cells or MDCK cells at 20,000 cells/well in a total volume of 100 µl EMEM with 10% FBS in flat bottomed 96-well microtitre plates. After 24 hours of incubation, cells were washed twice with PBS and then replenished with fresh EMEM before the addition of the compounds. After the addition of the compounds, the cells were further incubated at 37° C. with 5% $CO_2$ for 24 hours. MTT was added to each well to a final concentration of 0.5 mg/ml. The plates were further incubated at 37° C. with 5% $CO_2$ for 4 hours. At the end of the incubation period, 100 µl of 10% of lauryl sulfate (SDS) in 0.01M of hydrochloric acid (HCl) was added to each well to solubilize the cells. After overnight incubation, the plates were read at 570 nm with 640 nm as the reference wavelength. The median toxic concentration, $TC_{50}$, which represents the concentration of a compound required to reduce the MTT reading by 50%, was estimated from the MTT data.

Example 1

Synthesis of Compound 1 (YD-04)

Compound 1 was synthesized according to the synthetic scheme presented in Scheme 1. Examples of variations of the synthetic scheme for the synthesis of Compounds 2, 3, and 4 are presented in Schemes 2 and 3 to illustrate the slight variations in the synthesis of other analogs of Compound 1.

Synthesis of YD-041

To a solution of p-hydroxybenzaldehyde (3.7 g, 30.0 mmol) and triethylamine (6.3 mL, 45.0 mmol) in anhydrous dichloromethane (50 mL) was added dropwise a solution of t-butyldimethylsilyl chloride (6.8 g, 45.0 mmol) in anhydrous dichloromethane (50 mL). The resulting mixture was stirred at room temperature for 2 hours and then water (100 mL) was added. The organic layer was separated and the aqueous layer was extracted with dichloromethane. The combined organic layer was washed with water and saturated brine and dried over magnesium sulfate. After filtration and concentration, the residue obtained was further purified by column chromatography (petroleum ether:ethyl acetate=9:1) affording a yellow oil of crude product YD-041 (7.29 g).

Synthesis of Compound YD-042

YD-041 (1.18 g, 5 mmol) and hydroxylamine hydrochloride (1.15 g, 16.5 mmol) were dissolved in anhydrous ethanol (10 mL) at room temperature and then pyridine (20 mL) was added dropwise while stirring. The resulting mixture was stirred at room temperature for 30 minutes and then heated to reflux for 40 minutes. Upon completion, the reaction mixture was cooled to room temperature and a mixture of 37% hydrochloride solution (2 mL) and water (7.5 mL) was added. The resulting mixture was concentrated until one third of the total volume remained. After extraction with dichloromethane, the organic layer was washed with saturated brine and dried over magnesium sulfate. After removal of the solvent, the remaining residue was purified by column chromatography (petroleum ether:ethyl acetate=11:1) affording a yellow oil of YD-042 (0.862 g, 78%). $^1$H NMR (400 MHz, CDCl$_3$), δ 8.48 (br s, 1H, —OH), 8.10 (s, 1H, N═CH), 7.45 (d, J=8.6 Hz, 2H, Ar—H), 6.84 (d, J=8.6 Hz, 2H, Ar—H), 0.98 (s, 9H, —C(CH$_3$)$_3$), 0.21 (s, 6H, 2 SiCH$_3$).

Synthesis of Compound YD-043

YD-042 (810 mg, 3.2 mmol) was dissolved in anhydrous dimethylformamide (4 mL) and then cooled to 0° C. N-Chlorosuccinimide (NCS, 452 mg, 3.2 mmol) was added portionwise with stirring. The cooling bath was removed and the reaction mixture was stirred at room temperature for 1 hour. Upon completion, water in an amount 4 times the volume of the reaction mixture was added and the resulting mixture was extracted with diethyl ether. The organic layer was washed with water 3 times and dried over magnesium sulfate. After filtration and concentration, a yellow oil of crude YD-043 (884 mg, 96%) was obtained.

Synthesis of Compound YD-044

To a solution of YD-06 (737 mg, 3.8 mmol) in acetonitrile (40 mL) was added dropwise a solution of crude YD-043 (884 mg, 3.1 mmol) in acetonitrile (8 mL) at 0° C. The resulting mixture was stirred at 0° C. for 2 hours. Upon completion, ice water (4 mL) was added and most of the solvent was removed under reduced pressure. Water was added and the resulting mixture was extracted with diethyl ether. The organic layer was washed with water 3 times and saturated brine once and dried over magnesium sulfate. After filtration and concentration under reduced pressure, the residue was purified by column chromatography (petroleum ether:ethyl acetate=15:1) affording a yellow oil of YD-044 (627 mg, 52%). $^1$H NMR (400 MHz, CDCl$_3$), δ 7.48 (d, J=8.6 Hz, 2H, Ar—H), 6.89 (d, J=8.6 Hz, 2H, Ar—H), 2.69 (s, 3H, —CH$_3$), 1.44 (s, 9H, O—C(CH$_3$)$_3$), 0.99 (s, 9H, Si—C(CH$_3$)$_3$), 0.21 (s, 6H, 2 SiCH$_3$).

Synthesis of Compound YD-045

YD-044 (3.23 g, 8.3 mmol) was dissolved in trifluoroacetic acid (10 mL) and the resulting solution was stirred at room temperature for 30 minutes. Then trifluoroacetic acid was removed under reduced pressure and the residue was dissolved in diethyl ether. Petroleum ether was added to crystallize the product. After filtration and desiccation in vacuo, white flaky crystals of YD-045 (1.327 g, 48%) were obtained. m.p.=146-148° C.; $^1$H NMR (400 MHz, CDCl$_3$), δ 7.54 (d, J=8.6 Hz, 2H, Ar—H), 6.89 (d, J=8.6 Hz, 2H, Ar—H), 2.75 (s, 3H, —CH$_3$), 1.00 (s, 9H, Si—C(CH$_3$)$_3$), 0.23 (s, 6H, 2 SiCH$_3$).

Synthesis of Compound YD-046

To a solution of YD-045 (177 mg, 0.53 mmol) in anhydrous dichloromethane (8 mL) were added sequentially N,N-diisopropylethylamine (DIEA, 103 mg, 0.80 mmol), YD-05 (128 mg, 0.53 mmol) and 1-ethyl-3-(3-dimethylaminopropyl) carbodiimide (EDCI, 406 mg, 2.13 mmol). The resulting mixture was stirred at room temperature for 3 hours and then diluted with dichloromethane. The organic layer was separated, washed with 2 M sodium hydroxide solution, water and saturated brine, dried over sodium sulfate, filtrated and concentrated. The residue obtained was further purified by column chromatography (petroleum ether:ethyl acetate=3:1) affording light yellow needle crystals of YD-046 (141 mg, 48%). $^1$H NMR (400 MHz, CD$_3$COCD$_3$), δ 8.19 (d, J=2.7 Hz, 1H, Ar—H), 8.12 (dd, J=9, 2.7 Hz, 1H, Ar—H), 7.61 (d, J=8.7 Hz, 2H, Ar—H), 7.19 (d, J=9 Hz, 1H, Ar—H), 7.02 (d, J=8.7 Hz, 2H, Ar—H), 3.91 (br s, 2H, CH$_2$), 3.44 (br s, 2H, CH$_2$), 3.27 (br s, 2H, CH$_2$), 2.86 (br s, 2H, CH$_2$), 2.50 (s, 3H, —CH$_3$), 0.97 (s, 9H, Si—C(CH$_3$)$_3$), 0.23 (s, 6H, 2 SiCH$_3$).

Synthesis of Compound 1 (YD-04)

YD-046 (67 mg, 0.12 mmol) was dissolved in anhydrous tetrahydrofuran (4 mL), and tetra-n-butylammonium fluoride (TBAF, 63 mg, 0.24 mmol) was added. The resulting mixture was stirred at room temperature for 30 minutes. After concentration, the residue was purified by column chromatography (petroleum ether:ethyl acetate=1:1) affording a bright yellow powder of YD-04 (31 mg, 58%). Decomposed at 235-240° C.

1H NMR (400 MHz, DMSO-d6), δ 9.96 (br s, 1H, —OH), 8.23 (d, J=2.6 Hz, 1H, 1'-H), 8.14 (dd, J=9, 2.6 Hz, 1H, 2"-H), 7.44 (d, J=8.7 Hz, 2H, 2-H, 3-H), 7.21 (d, J=9 Hz, 1H, 3'-H), 6.89 (d, J=8.3 Hz, 2H, 1-H, 4-H), 3.82 (br s, 2H, CH$_2$), 3.36 (br s, 2H, CH$_2$), 3.21 (br s, 2H, CH$_2$), 2.89 (br s, 2H, CH$_2$), 2.46 (s, 3H, —CH$_3$).

$^{13}$C NMR (100 MHz, DMSO-d6) δ 168.3, 161.5, 159.3, 159.2, 154.0, 141.8, 128.7, 126.3, 125.9, 123.6, 120.6, 118.5, 115.8, 110.4, 50.1, 49.7, 46.2, 41.2, 11.3; LRMS (API-ES): 443 (M++H).

Example 2

Synthesis of Compound 2 (YD-01)

The synthesis of Compounds 2 (YD-01) is shown structurally in Scheme 2.

Synthesis of Compound YD-011

Benzaldehyde (10.60 g, 0.10 mol) and hydroxylamine hydrochloride (22.94 g, 0.33 mol) were dissolved in 90% ethanol (330 mL). The pH of this solution was adjusted to 5 by adding sodium hydroxide powder. The resulting solution was stirred at room temperature for 30 min and heated to reflux for an additional 30 min. The reaction mixture was cooled to ambient temperature, added to a mixture of concentrated hydrochloric acid (40 mL) and water (150 mL), and concentrated to ⅓ of the original volume. The concentrated mixture was extracted with dichloromethane, and the organic layer was washed with saturated brine, dried over anhydrous magnesium sulfate, and evaporated under vacuum to give a yellow crude oil. The crude oil was purified by vacuum distillation (40 mm Hg, 150-155° C.) to afford a light yellow oil, YD-011 (9.87 g, 82% yield), which formed off-white crystals upon freezing. Both cis and trans isomers were detected by TLC.

$^1$H-NMR (400 MHz, CDCl$_3$) δ 9.01 (br s, 1H, —OH), 8.17 (s, 1H, =CH), 7.59-7.56 (m, 2H, Ar—H), 7.40-7.35 (m, 3H, Ar—H).

Synthesis of Compound YD-012

To a solution of YD-011 (2 g, 16.53 mmol) in anhydrous dichloromethane at 0° C. was added N-chlorosuccinimide (NCS, 8.79 g, 66 mmol) in portions with stirring. The mixture was warmed to ambient temperature and stirred for 2 hours. Water (50 mL) was added to the reaction mixture and the layers were separated. The aqueous layer was extracted with dichloromethane (20 mL×3), and the combined organic layer was washed with saturated brine, dried over anhydrous magnesium sulfate, filtered, and concentrated under vacuum. The crude products were subjected to column chromatography, eluting with a gradient of decreasing petroleum ether in ethyl acetate (100:150:1), to give YD-012 (1.02 g, 40% yield). The cis and trans isomers were detected by TLC. Due to the instability of YD-012 it was used directly in the next step without further purification.

Synthesis of Compound YD-06

To a solution of t-butyl acetoacetate (5.2 mL) in ether (100 mL) was added dropwise a solution of potassium hexamethyldisilazide (1 M, 28.64 mL) in tetrahydrofuran (THF). The reaction mixture was concentrated and precipitated by adding n-hexane. The precipitate were filtered and dried to give crude product YD-06.

Synthesis of Compound YD-013

The crude YD-06 (1.0 g, 5.1 mmol) was dissolved in acetonitrile (50 mL), and the mixture was cooled to 0° C. A solution of compound YD-012 (0.65 g, 4.2 mmol) in acetonitrile (10 mL) was added dropwise to the solution of YD-06 with stirring. The reaction mixture was stirred for 2 hours at 0° C. and ice water (4 mL) was added. The mixture was evaporated under vacuum. The residue was redissolved in water and extracted with dichloromethane. The organic layer was washed with saturated brine, dried over anhydrous magnesium sulfate, filtered, and concentrated under vacuum to give a crude residue, which was purified by column chromatography with petroleum ether (60-90° C.) as eluent to give YD-013 (510 mg, 47% yield) as an off-white solid. $^1$H-NMR (400 MHz, CDCl$_3$) δ 7.59-7.56 (m, 2H, Ar—H), 7.47-7.40 (m, 3H, Ar—H), 2.71 (s, 3H, —CH$_3$), 1.41 (s, 9H, —C(CH$_3$)$_3$).

Synthesis of Compound YD-014

Compound YD-013 (186 mg, 0.718 mmol) was dissolved in trifluoroacetic acid (5 mL) and the solution was stirred for 4 hour at room temperature. The resulting solution was evaporated under vacuum to remove trifluoroacetic acid. Dichloromethane was added and the solution was redistilled two times. The residue was dissolved in ether, and recrystallization was performed by adding petroleum ether. The white crystalline compound YD-014 was isolated by filtration and dried under vacuum. The mother liquor was concentrated, and purification by column chromatography eluting with 1% volume glacial acetic acid in petroleum ether-ethyl acetate (3:1) gave YD-014 as a white solid. The combined weights of the crystalline compounds were 115 mg (79% yield). $^1$H-NMR (400 MHz, CDCl$_3$) δ 7.65-7.62 (m, 2H, Ar—H), 7.51-7.42 (m, 3H, Ar—H), 2.77 (s, 3H, —CH$_3$).

Synthesis of Compound YD-05

To a solution of piperazine (3.73 g, 43.4 mmol) in N,N-dimethylformamide (11 mL) was added dropwise an N,N-dimethylformamide (15 mL) solution of 3,4-dichloronitrobenzene (1.64 g, 8.6 mmol) with stirring at room temperature. The resulting mixture was heated to 100° C. and maintained at that temperature for 5 hours. The reaction mixture was cooled to room temperature and was concentrated under vacuum to remove N,N-dimethylformamide. The resulting residue was diluted with dichloromethane (25 mL). The organic layer was washed with saturated aqueous sodium bicarbonate solution, dried with anhydrous sodium sulfate, filtered, and concentrated. The recrystallization of the residue from chloroform and methanol (3:1) gave a yellow crystalline compound YD-05 (1.77 g, 85% yield). $^1$H NMR (400 MHz, CDCl$_3$) δ 8.24 (d, J=2.6 Hz, 1H, Ar—H), 8.09 (dd, J=9, 2.6 Hz, 1H, Ar—H), 7.04 (d, J=9 Hz, 1H, Ar—H), 3.20-3.18 (m, 4H, 2CH$_2$), 3.08-3.06 (m, 4H, 2CH$_2$), 1.93 (br s, 1H, NH).

Synthesis of Compound 2 (YD-01)

To a solution of YD-014 (320 mg, 1.58 mmol) in anhydrous dichloromethane (10 mL) was added in sequence diisopropylethylamine (DIEA, 305 mg, 2.36 mmol), YD-05 (380 mg, 1.58 mmol) and 1-(3-dimethylaminopropyl)-3-ethylcarbodiimide (EDCI, 1.2 g, 6.30 mmol). The resulting mixture was stirred at room temperature for 2 hours. The reaction mixture was diluted with dichloromethane, and washed in sequence with aqueous sodium hydroxide (2 M), water and saturated brine. The organic layer was dried over anhydrous sodium sulfate, filtered, and concentrated. The residue was purified by column chromatography eluting with petroleum ether in ethyl acetate (3:1) to give YD-01 (290 mg, 43% yield) as a light yellow solid.

$^1$H-NMR (400 MHz, DMSO-d6) δ 8.23 (d, 111, J=2.6 Hz, 1'-H), 8.15 (dd, 1H, J=9, 2.6 Hz, 2'-H), 7.63-7.60 (m, 2H, 1-H, 5-H), 7.55-7.52 (m, 3H, 2-H, 3-H, 4-H), 7.20 (d, 1H, J=9 Hz, 3'-H), 3.81 (br s, 2H, CH$_2$), 3.39 (br s, 21-1, CH$_2$), 3.20 (br s, 2H, CH$_2$), 2.85 (br s, 2H, CH$_2$), 2.50 (s, 3H, —CH$_3$);

$^{13}$C-NMR (100 MHz, DMSO-d6) δ 168.8, 161.2, 159.6, 153.9, 141.9, 130.2, 129.1, 127.9, 127.3, 126.3, 125.9, 123.7, 120.6, 110.7, 50.1, 49.7, 46.3, 41.3, 11.4; LRMS (API-ES): 427 (M$^+$+H).

Example 3

Synthesis of Compound 3 (YD-07)

The synthesis of Compound 3 (YD-07) is shown structurally in Scheme 3.

Synthesis of Compound YD-031 p-Nitrobenzaldehyde (4.53 g, 0.03 mol) and hydroxylamine hydrochloride (6.87 g, 0.099 mol) were dissolved in 90% ethanol (100 mL) at room temperature. The pH of the reaction mixture was adjusted to 5 by adding sodium hydroxide powder and the resulting solution was stirred at room temperature for 30 minutes before being heated to reflux for 4 hours. Upon completion, the reaction mixture was cooled to room temperature and the ethanol was removed under reduced pressure. Water was added and the resulting mixture was extracted with dichloromethane. The combined organic layer was washed with saturated brine and dried over magnesium sulfate. After removing the solvent, a yellow amorphous powder of YD-031 (4.831 g, 97%) of spectroscopic purity was obtained. m.p. 127-129° C.; 1H NMR (400 MHz, CDCl$_3$) δ 8.26 (d, J=8.8 Hz, 2H, Ar—H), 8.21 (s, 1H, N=CH), 7.98 (s, 1H, —OH), 7.75 (d, J=8.8 Hz, 2H, Ar—H).

Synthesis of Compound YD-032

YD-031 (887 mg, 5.3 mmol) was dissolved in anhydrous dimethylformamide (4.6 mL) and the solution was cooled to 0° C. N-Chlorosuccinimide (800 mg, 6.0 mmol) was added portion-wise with stirring. The cooling bath was removed and the resulting mixture was stirred at room temperature for 4 hours. Upon completion, ice water (20 mL) was added and the resulting mixture was extracted with diethyl ether. The organic layer was washed with water 3 times and saturated brine once, and dried over magnesium sulfate. Removing the solvent after filtration afforded a white solid of YD-032 (1.064 g, 100%). $^1$H NMR (400 MHz, CDCl$_3$), δ 8.37 (s, 1H, —OH), 8.27 J=8.8 Hz, 2H, Ar—H), 8.04 (d, J=8.8 Hz, 2H, Ar—H).

Synthesis of Compound YD-033

To a solution of crude YD-06 (1.213 g, 6.2 mmol) in acetonitrile (60 mL) was added a solution of crude YD-032 (1 g, 5.0 mmol) in acetonitrile (25 mL) at 0° C. while stirring. The resulting solution was stirred at 0° C. for 2 hours. Upon completion, ice water (4 mL) was added and most of the solvent was removed under reduced pressure. The remaining liquid was diluted with water and extracted with dichloromethane. The organic layer was washed with saturated brine and dried over magnesium sulfate. After filtration and removing the solvent, the residue was purified by column chromatography (petroleum ether:ethyl acetate=10:1) affording a light yellow cubic crystal of YD-033 (1.239 g, 78%). imp. 86-87° C.; $^1$H NMR (400 MHz, CDCl$_3$) δ 8.31 (d, J=8.8 Hz, 2H, Ar—H), 7.81 (d, J=8.8 Hz, 2H, Ar—H), 2.75 (s, 3H, —CH$_3$), 1.46 (s, 9H, O—C(CH$_3$)$_3$).

Synthesis of Compound YD-034

YD-033 (100 mg, 0.33 mmol) and Tin(II) chloride dihydrate (371 mg, 1.64 mmol) were dissolved in anhydrous ethanol (7 mL) and the resulting solution was heated at reflux for 1.5 hours. The reaction mixture was cooled to room temperature and an appropriate amount of ice water was added. The pH of the resulting mixture was adjusted to 8 by the addition of 20% aqueous sodium carbonate solution. After extraction with ethyl acetate, the organic layer was washed with brine and dried over sodium sulfate. The residue obtained after filtration and concentration was purified using a silica gel column (petroleum ether:ethyl acetate=5:1) affording white needle crystals YD-034 (72 mg, 80%). $^1$H NMR (400 MHz, CDCl$_3$) δ 7.42 (d, 3=8.6 Hz, 2H, Ar—H), 6.69 (d, J=8.6 Hz, 2H, Ar—H), 3.78 (br s, 2H, NH$_2$), 2.66 (s, 3H, —CH$_3$), 1.47 (s, 9H, O—C(CH$_3$)$_3$).

Synthesis of Compound YD-038

YD-034 (1.0 g, 3.65 mmol) was dissolved in trifluoroacetic acid (5 mL) and stirred for 1 hour at room temperature. Trifluoroacetic acid was removed under reduced pressure and the residue was azeotroped with dichloromethane twice affording a white solid of crude YD-038 (810 mg).

Synthesis of Compound 3 (YD-03)

To a solution of crude YD-038 (157 mg, 0.72 mmol) in anhydrous dichloromethane (8 mL) were added sequentially N,N-diisopropylethylamine (DIEA, 138 mg, 1.08 mmol), YD-05 (207 mg, 0.86 mmol) and EDCI (550 mg, 2.88 mmol). The resulting mixture was stirred at room temperature for 4 hours and then diluted with dichloromethane. This mixture was washed with 2 M sodium hydroxide solution, water and saturated brine. The organic layer was dried over sodium sulfate, filtrated and concentrated. The residue obtained was purified by column chromatography (petroleum ether:ethyl acetate=2:1) affording a bright yellow powder of YD-03 (173 mg, 49%).

$^1$H NMR (400 MHz, DMSO-d6), δ 8.24 (d, J=2.7 Hz, 1H, 1'-H), 8.15 (dd, =9, 2.7 Hz, 1H, 2'-H), 7.28 (d, J=8.6 Hz, 2 μl, 2-H, 3-H), 7.19 (d, J=9 Hz, 1H, 3'-H), 6.63 (d, J=8.6 Hz, 2H, 1-H, 4-H), 5.60 (br s, 2H, NH$_2$), 3.81 (br s, 2H, CH$_2$), 3.34 (br s, 2H, CH$_2$), 3.20 (br s, 2H, CH$_2$), 2.86 (br s, 2H, CH$_2$), 2.42 (s, 3H, —CH$_3$);

$^{13}$C NMR (100 MHz, DMSO-d6), δ 167.9, 161.8, 159.5, 154.0, 150.7, 141.9, 128.2, 126.4, 125.9, 123.7, 120.6, 1145, 113.7, 110.2, 50.0, 49.8, 46.3, 41.2, 11.4; LRMS (API-ES): 442 (M++H).

Example 4

Synthesis of Compound 4 (YD-07)

Compound YD-03 (50 mg, 0.1134 mmol) was dissolved in 6 M sulfuric acid (1 mL) and the resulting solution was cooled to 0° C. A solution of sodium nitrite (7.2 mg, 0.136 mmol) in water (0.5 mL) was added dropwise while stirring. The resulting mixture was stirred for another 30 min while maintaining the temperature below 5° C. A solution of sodium azide (125 mg, 1.923 mmol) in water (1 mL) was added and the temperature was raised to room temperature. The mixture was stirred for another 2 hours before dilution with water. After extraction with ethyl acetate, the combined organic layer was washed with saturated brine and dried over sodium sulfate. After concentration, the residue obtained was purified by column chromatography (petroleum:ethyl acetate=4:1) affording a bright yellow powder of YD-07 (38 mg, 72%). $^1$H NMR (400 MHz, DMSO-d6), δ 8.24 (d, J=2.7 Hz, 1H, 1'-H), 8.16 (dd, J=9, 2.7 Hz, 1H, 2'-H), 7.66 (d, J=8.6 Hz, 2H, 2-H, 3-H), 7.28 (d, J=8.6 Hz, 2H, 1-H, 4-H), 7.24 (d, J=9 Hz, 1H, 3'-H), 3.83 (br s, 2H, CH$_2$), 3.44 (br s, 2H, CH$_2$), 3.24 (br s, 2H, CH$_2$), 2.95 (br s, 2H, CH$_2$), 2.49 (s, 3H, —CH$_3$);

$^{13}$C NMR (100 MHz, DMSO-d6) δ 168.7, 161.1, 158.9, 154.0, 141.8, 141.4, 128.9, 126.3, 125.9, 124.5, 123.7, 120.7, 119.9, 110.5, 50.3, 49.7, 46.3, 41.3, 11.4; LRMS (API-ES): 468 (M++H).

Example 5

Synthesis of Compounds 5-10

Compound 5 was prepared according to Scheme 2, but starting with o-chlorobenzaldehyde instead of benzaldehyde.

Compound 6 was prepared according to Scheme 2 as for compound 5, but using a 2-methyl derivative of YD-05 prepared from 2-methylpiperazine instead of piperazine.

Compound 7 was prepared according to Scheme 2 as for compound 6 using Scheme 2, but starting from benzaldehyde instead of o-chlorobenzaldehyde.

Compound 8 was prepared according to Scheme 2 as for Compound 2 but using 4-chloronitrobenzene instead of 3,4-dichloronitrobenzene.

Compound 9 was prepared according to Scheme 2 as for compound 2, but using 2,6-dichlorobenzaldehyde as starting material instead of benzaldehyde.

Compound 10 was prepared according to Scheme 2 as for Compound 8, but using 2,3-dichloronitrobenzene instead of 3,4-dichloronitrobenzene as starting material.

Example 6

Antiviral Activity of Compounds 1-10

In order to measure quantitatively the protection conferred by Compounds 1-10, plaque reduction assays were performed. The compounds inhibited influenza A virus plaque formation in MDCK cells with EC$_{50}$ of 0.05, 0.06, 0.56, 0.25, 0.04, 0.21, 0.8, 5.1, 12, and 25 μM for Compounds 1 to 10 respectively (see FIGS. 1B, 2B, 3B, 4B, 5B, 6B, 7B, 8B, 9B, and 10B).

Compounds 1 to 10 were assayed for cytotoxicity on MDCK and Vero cells. Compound concentrations tested were ranging from 0 to 250 μM and the results are shown in Table 1. The results indicate that the TC50 of Compounds 1 to 10 is above 250 μM in both MDCK and Vero cells. The selectivity index (SI) that was defined by the ratio of TC50/EC50 in MDCK cells for Compounds 1 to 10 is presented in Table 1. The results show that this family of amides is generally non-toxic to mammalian cells.

TABLE 1

Antiviral activity of Compounds 1-10

| Compound | $EC_{50}$ by PRA (μM) | $TC_{50}$ in MDCK cells (μM) | $TC_{50}$ in Vero cells (μM) | Selective Index (SI) |
|---|---|---|---|---|
| 1 | 0.05 | >250 | >250 | >5000 |
| 2 | 0.06 | >250 | >250 | >4167 |
| 3 | 0.056 | >250 | >250 | >4464 |
| 4 | 0.25 | >250 | >250 | >1000 |
| 5 | 0.04 | >250 | >250 | >6250 |
| 6 | 0.21 | >250 | >250 | >1190 |
| 7 | 0.8 | >250 | >250 | >313 |
| 8 | 5.1 | >250 | >250 | >49 |
| 9 | 12 | >250 | >250 | >21 |
| 10 | 25 | >250 | >250 | >10 |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:
1. A compound of formula VI:

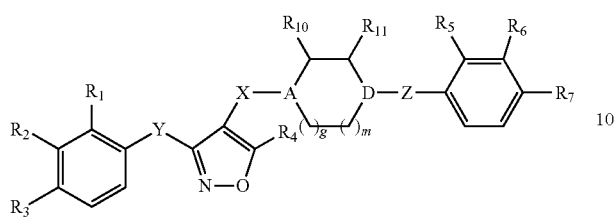

(formula VI)

X, Y, and Z are independently absent or selected from the group consisting of —C(=O)—, —S(=O)—, —SO$_2$—, —N(R$_{12}$)—, —C(R$_{13}$)=C(R$_{14}$)—, and —C(R$_{15}$R$_{16}$)$_n$—;
n, g, and m are independently 0 to 6;
A and D are independently selected from nitrogen or CR$_{17}$;
wherein R$_1$, R$_2$, R$_4$, R$_5$, R$_6$ and R$_{10}$-R$_{17}$ are independently selected from hydrogen; halo; hydroxyl; substituted or unsubstituted, linear or branched C$_1$-C$_6$ alkyl; substituted or unsubstituted, linear or branched C$_1$-C$_6$ alkenyl; substituted or unsubstituted, linear or branched C$_1$-C$_6$ alkynyl; or substituted or unsubstituted, linear or branched C$_1$-C$_6$ alkoxy; amino; azide; cyano; nitro; nitrile; isonitrile; amide; carboxylate; urea; guanidine; isocyanate; isothiocyanate; and thioether, and
R$_7$ is selected from halo; hydroxyl; substituted or unsubstituted, linear or branched C$_1$-C$_6$ alkyl; substituted or unsubstituted, linear or branched C$_1$-C$_6$ alkenyl; substituted or unsubstituted, linear or branched C$_1$-C$_6$ alkynyl; or substituted or unsubstituted, linear or branched C$_1$-C$_6$ alkoxy; amino; azide; cyano; nitro; nitrile; isonitrile; amide; carboxylate; urea; guanidine; isocyanate; isothiocyanate; and thioether.
2. The compound of claim 1, wherein A and D are nitrogen.
3. The compound of claim 1, wherein R$_4$ and R$_{10}$ are independently hydrogen or methyl.
4. The compound of claim 3, wherein R$_4$ is methyl and R$_{10}$ is hydrogen.
5. The compound of claim 3, wherein R$_{10}$ is a methyl group and R$_{11}$ is hydrogen.
6. The compound of claim 3, wherein R$_{10}$ and R$_{11}$ are both hydrogen.
7. The compound of claim 1, wherein Y and Z are absent, g and m are 1, and X is C=O.
8. The compound of claim 1, wherein R$_1$-R$_3$ and R$_5$-R$_7$ are independently selected from halo and nitro.
9. A compound of selected from the group consisting of:
[4-(2-chloro-4-nitro-phenyl)-piperazin1-yl]-[3-(4-hydroxy-phenyl)-5-methylisoxazol-4-yl]-methanone;
[4-(2-chloro-4-nitro-phenyl)-piperazin-1-yl]-[3-phenyl-5-methyl-isoxazol-4-yl]-methanone;
[4-(2-chloro-4-nitro-phenyl)-piperazin-1-yl]-[3-(4-amino-phenyl)-methylisoxazol-4-yl]-methanone;
[4-(2-chloro-4-nitro-phenyl)-piperazin-1-yl]-[3-(4-azido-phenyl)-5-methylisoxazol-4-yl]-methanone;
[4-(2-chloro-4-nitro-phenyl)-piperazin-1-yl]-[3-(2-chloro-phenyl)-5-methylisoxazol-4-yl]-methanone;
[4-(2-chloro-4-nitro-phenyl)-2-methyl-piperazin-1-yl]-[3-(2-chloro-phenyl)-5-methyl-isoxazol-4-yl]-methanone;
[4-(2-chloro-4-nitro-phenyl)-2-methyl-piperazin-1-yl]-[3-phenyl-5-methylisoxazol-4-yl]-methanone;
[4-(4-nitro-phenyl)-piperazin-1-yl]-[3-(2-chloro-phenyl)-5-methyl-isoxazol-4-yl]-methanone;
and [4-(4-nitro-phenyl)-piperazin-1-yl]-[3-(2,6-dichlorophenyl)-5-methyl-isoxazol-4-yl]-methanone.
10. A compound of formula (III):

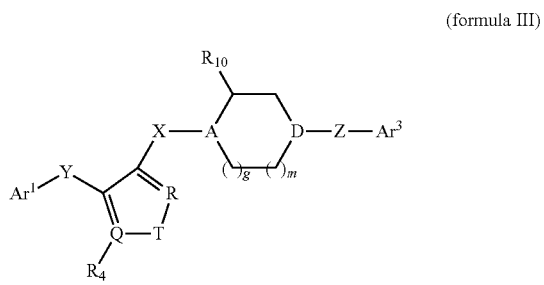

(formula III)

wherein T, Q, and R are independently selected from C(R$_8$R$_9$), nitrogen, oxygen, phosphorous, silicon, sulfur, and arsenic;
wherein R$_4$ and R$_8$-R$_9$ are independently selected from hydrogen; halo; hydroxyl; substituted or unsubstituted, linear or branched C$_1$-C$_6$ alkyl; substituted or unsubstituted, linear or branched C$_1$-C$_6$ alkenyl; substituted or unsubstituted, linear or branched C$_1$-C$_6$ alkynyl; or substituted or unsubstituted, linear or branched C$_1$-C$_6$ alkoxy; amino; azide; cyano; nitro; nitrile; isonitrile; amide; carboxylate; urea; guanidine; isocyanate; isothiocyanate; and thioether;
wherein Ar$^1$ and Ar$^a$ are each independently substituted or unsubstituted aryl or heteroaryl groups;
X, Y, and Z are independently absent or selected from the group consisting of —C(=O)—, —S(=O)—, —SO$_2$—, —N(R$_{12}$)—, —C(R$_{13}$)=C(R$_{14}$)—, and —C(R$_{15}$R$_{16}$)$_n$—;
n, g and m are independently 0 to 6;
A and D are independently selected from nitrogen or CR$_{17}$;
wherein when Ar$^3$ is phenyl, and the phenyl group is substituted at the para position, the substituent is selected from the group consisting of halo; hydroxyl; substituted or unsubstituted, linear or branched C$_1$-C$_6$ alkyl; substituted or unsubstituted, linear or branched C$_1$-C$_6$ alkenyl; substituted or unsubstituted, linear or branched C$_1$-C$_6$ alkynyl; or substituted or unsubstituted, linear or branched C$_1$-C$_6$ alkoxy; amino; azide; cyano; nitro; nitrile; isonitrile; amide; carboxylate; urea; guanidine; isocyanate; isothiocyanate; and thioether, or the phenyl group comprises a nitro group,
R$_{12}$-R$_{17}$ are independently selected from hydrogen; halo; hydroxyl; substituted or unsubstituted, linear or branched C$_1$-C$_6$ alkyl; substituted or unsubstituted, linear or branched C$_1$-C$_6$ alkenyl; substituted or unsubstituted, linear or branched C$_1$-C$_6$ alkynyl; or substituted or unsubstituted, linear or branched C$_1$-C$_6$ alkoxy; amino; azide; cyano; nitro; nitrile; isonitrile; amide; carboxylate; urea; guanidine; isocyanate; isothiocyanate; and thioether; and
R$_{10}$ is independently selected from hydrogen; halo; hydroxyl; substituted or unsubstituted, linear or branched C$_1$-C$_6$ alkyl; substituted or unsubstituted, linear or branched C$_1$-C$_6$ alkenyl; substituted or unsubstituted, linear or branched C$_1$-C$_6$ alkynyl; or substituted or unsubstituted, linear or branched C$_1$-C$_6$ alkoxy; amino; azide; cyano; nitro; nitrite; isonitrile; amide; carboxylate; urea; guanidine; isocyanate; isothiocyanate; and thioether.

11. The compound of claim 10, wherein $Ar^1$ is substituted with hydrogen, hydroxyl, nitro, amino, or azide; X is C=O; Y and Z are absent, and $Ar^3$ is substituted with a halo group, a nitro group, or a combination of a halo and nitro group.

12. The compound of claim 10, wherein Q is carbon, T is oxygen, and R is nitrogen.

13. The compound of claim 10, wherein A and D are nitrogen.

14. The compound of claim 10, wherein $R_4$ and $R_{10}$ are independently hydrogen or methyl.

15. The compound of claim 10, wherein $R_4$ is methyl and $R_{10}$ is hydrogen.

16. The compound of claim 10, wherein A and D are both nitrogen.

17. The compound of claim 10, wherein $R_{10}$ is a methyl group and $R_{11}$ is hydrogen.

18. The compound of claim 10, wherein $R_{10}$ and $R_{11}$ are both hydrogen.

19. The compound of claim 10, wherein Y and Z are absent, g and m are 1, and X is C=O.

\* \* \* \* \*

SEQUENCE LISTING

```
<160> NUMBER OF SEQ ID NOS: 4

<210> SEQ ID NO 1
<211> LENGTH: 32
<212> TYPE: PRT
<213> ORGANISM: Influenza A virus

<400> SEQUENCE: 1

Val Tyr Gly Ser Ala Val Ala Ser Gly Tyr Asp Phe Glu Arg Glu Gly
1               5                   10                  15

Tyr Ser Leu Val Gly Ile Asp Pro Phe Arg Leu Leu Gln Asn Ser Gln
            20                  25                  30

<210> SEQ ID NO 2
<211> LENGTH: 6
<212> TYPE: PRT
<213> ORGANISM: Influenza A virus

<400> SEQUENCE: 2

Glu Leu Ser Asp Glu Lys
1               5

<210> SEQ ID NO 3
<211> LENGTH: 5
<212> TYPE: PRT
<213> ORGANISM: Influenza A virus

<400> SEQUENCE: 3

Ala Thr Glu Ile Arg
1               5

<210> SEQ ID NO 4
<211> LENGTH: 26
<212> TYPE: PRT
<213> ORGANISM: Influenza A virus

<400> SEQUENCE: 4

Ala Thr Glu Ile Arg Ala Ser Val Gly Lys Met Ile Asp Gly Ile Gly
1               5                   10                  15

Arg Phe Tyr Ile Gln Met Cys Thr Glu Leu
            20                  25
```